(12) United States Patent
Ohgi et al.

(10) Patent No.: US 8,691,970 B2
(45) Date of Patent: Apr. 8, 2014

(54) PHOSPHORAMIDITE COMPOUND AND METHOD FOR PRODUCING OLIGO-RNA

(75) Inventors: Tadaaki Ohgi, Tsuchiura (JP); Kouichi Ishiyama, Tsukuba (JP); Yutaka Masutomi, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 689 days.

(21) Appl. No.: 11/574,308

(22) PCT Filed: Aug. 25, 2005

(86) PCT No.: PCT/JP2005/015420
§ 371 (c)(1),
(2), (4) Date: Aug. 3, 2007

(87) PCT Pub. No.: WO2006/022323
PCT Pub. Date: Mar. 2, 2006

(65) Prior Publication Data
US 2007/0282097 A1    Dec. 6, 2007

(30) Foreign Application Priority Data

Aug. 26, 2004  (JP) ................. 2004-246185
Apr. 7, 2005   (JP) ................. 2005-110817
Jul. 1, 2005   (JP) ................. 2005-193313

(51) Int. Cl.
C07H 19/04    (2006.01)
C07H 21/02    (2006.01)

(52) U.S. Cl.
USPC ................. 536/26.1; 536/23.1; 536/25.31

(58) Field of Classification Search
USPC ................... 536/23.1, 26.1, 25.31
See application file for complete search history.

(56) References Cited

U.S. PATENT DOCUMENTS

| | | | |
|---|---|---|---|
| 3,956,500 | A | 5/1976 | Durden, Jr. et al. |
| 4,629,814 | A | 12/1986 | James |
| 4,925,856 | A | 5/1990 | Harris, III et al. |
| 5,504,263 | A | 4/1996 | Burgess et al. |
| 5,637,776 | A | 6/1997 | Burgess et al. |
| 5,696,308 | A | 12/1997 | Burgess et al. |
| 5,750,807 | A | 5/1998 | Burgess et al. |
| 2004/0192924 | A1 | 9/2004 | Meyer et al. |

FOREIGN PATENT DOCUMENTS

| | | |
|---|---|---|
| JP | 03-074398 | 3/1991 |
| WO | 03/035617 A2 | 5/2003 |

OTHER PUBLICATIONS

Pitsch et al. Helvetica Chimica Acta, 2001, 84, p. 3773-3795.*
Soil et al. RNA, 2001, Pergamon, Elsevier Science, 1st ed., p. 91-100.*
Pfleiderer et al., Acta Biochimica Polonica, 1996, 43(1), p. 37-44.*
Wada et al., Tetrahedron Letters, 1995, 36(10), p. 1683-1684.*
N. Usman, et al., Automated Chemical Synthesis of Long Oligoribonucleotides Using 2'-O-Silylated Ribonucleoside 3"-O-Phosphoramidites on a Controlled-Pore Glass Support: Synthesis of a 43-Nucleotide Sequence Similar to the 3'-Half Molecule of an *Escherichia coli* Formylmethionine tRNA, Journal of American Chemical Society, 1987, vol. 109, pp. 7845-7854.
Stefan Matysiak, et al., Acetals as New 2'-0-Protecting Functions for the Synthesis of Oligoribonucleotides: Synthesis of Uridine Building Blocks and Evaluation of Their Relative Acid Stability, Helvetica Chemica Acta, vol. 81, 1998, pp. 1545-1566.

(Continued)

*Primary Examiner* — Eric S Olson
*Assistant Examiner* — Jonathan S Lau
(74) *Attorney, Agent, or Firm* — McDermott Will & Emery LLP

(57) ABSTRACT

An object of the present invention is to provide a useful and novel phosphoramidite compound for the synthesis of oligo-RNA.
A phosphoramidite compound represented by general formula (1),

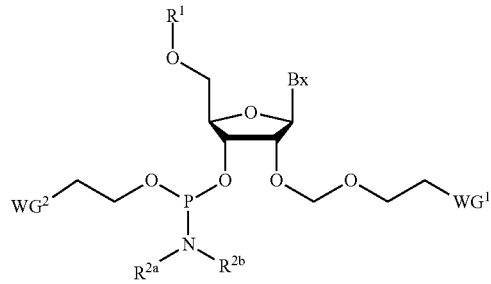

(1)

wherein:
$B_X$ represents a nucleobase optionally having a protecting group; and
$R^1$ is a substituent represented by general formula (2),

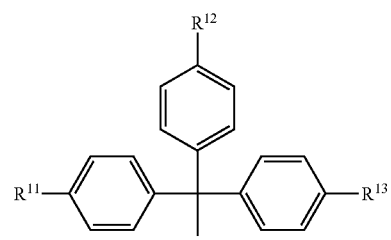

(2)

wherein:
$R^{11}$, $R^{12}$ and $R^{13}$ are the same or different and each represents hydrogen or alkoxy;
$R^{2a}$ and $R^{2b}$ are the same or different and each represents alkyl, or $R^{2a}$ and $R^{2b}$ taken together with the adjacent nitrogen atom may form a 5- to 6-membered saturated amino cyclic group, the amino cyclic group optionally having an oxygen or sulfur atom as a ring-composing member in addition to the adjacent nitrogen atom; and
$WG^1$ and $WG^2$ are the same or different and each represents an electron-withdrawing group.

4 Claims, 1 Drawing Sheet

(56) References Cited

OTHER PUBLICATIONS

Takeshi Wada, RNA Interference (RNAi) and Chemical Synthesis of RNA, Bio Industry, 2004, vol. 21, No. 1, pp. 17-24.

Tadashi Umemoto, et al., Oligoribonucleotide synthesis by the use of 1-(2-cyanoethoxy)ethyl (CEE) as a 2'-hydroxy protecting group, Tetrahedron Letters, vol. 45, 2004, pp. 9529-9531.

George A. Olah, et al., Carcinogen Chemistry. 4. (Haloalkyl)oxonium and (Haloalkyl)carboxonium Ions. Preapration, Nuclear Magnetic Resonance Structural Study, and Alkylating Ability, Journal of Organic Chemistry, 1981, vol. 46, No. 3, pp. 571.

J.F. Normant, et al., Reactivite des vinylcuivres. Application a la synthese d'alcools allyliques substitues stereospecifiquement, Tetrahedron Letters, No. 26, pp. 2407-2408, 1973.

Hisao Kitano, et al., Preparation of Some Fluoroethanol Derivatives, Journal of the Chemical Society of Japan, Industrial Chemistry Section, (Kogyo Kagaku Zasshi), vol. 58, pp. 355-357, 1955.

A. Stutz et al., Automated RNA-Synthesis with Photocleavable Sugar and Nucleobase Protecting Groups,Synlett, No. S1, pp. 930-934, 1999.

F. E. Wincott et al., 2'-(Trimethylsilyl)ethoxymethyl Protection of the 2'-Hydroxyl Group in Oligoribonucleotide Synthesis, Tetrahedron Letters, vol. 35, No. 37, pp. 6827-6830, 1994.

S. Pitsch et al., Fast and Reliable Automated Synthesis of RNA and Partially 2'-O-Protected Precursors ('Caged RNA') Based on Two Novel, Orthogonal 2'-O-Protecting Groups, Helvetica Chimica Acta, vol. 82, pp. 1753-1761, 1999.

S. Zavgorodny, et al., 1-Alkythioalkylation of Nucleoside Hydroxyl Functions and Its Synthetic Applications: A New Versatile Method in Nucleoside Chemistry, Tetrahedron Letters, vol. 32, No. 51, pp. 7593-7596, 1991.

G. R. Gough et al., p-Nitrobenzyloxymethyl: A New Fluoride-Removable Protecting Group for Ribonucleoside 2'-Hydroxyls, Tetrahedron Letters, vol. 37, No. 7, pp. 981-982, 1996.

S. Pitsch, 159. An Efficient Synthesis of Enantiomeric Ribonucleic Acids from D-Glucose, Helvetica Chimica Acta, vol. 80, pp. 2286-2314, 1997.

Supplementary European Search Report for EP 05 78 0944 (Mar. 5, 2009).

Ohgi, et al. "A New RNA Synthetic Method with a 2'-0-(2-Cyanoethoxymethyl) Protecting Group" Organic Letters, American Chemical Society, (7)16:3477-80 (Jul. 7, 2005).

Umemoto, et al. "Oligoribonucleotide synthesis by the use of 1-(2-cyanoethoxy)ethyl (CEE) as a 2'-hydroxy protecting group" Tetrahedron Letters, (45)52:9529-31 (Nov. 11, 2004).

Wu, et al. "Synthesis of 5'-C- and 2'-O-(Bromoalkyl)-Substituted Ribonucleoside Phosphoramidites for the Post-synthetic Functionalization of Oligonucleotides on Solid Support" Helvetica Chimica Acta, vol. 83 (2000), pp. 1127-1144.

Matysiak, et al. "Acetals as New 2'-O-Protecting Functions for the Synthesis of Oligoribonucleotides: Synthesis of Uridine Building Blocks and Evaluation of Their Relative Acid Stability"; Helvetica Chimica Acta, vol. 81, pp. 1545-1566, Published 1998.

Database Caplus (online), Chemical Abstracts Service, ASTROM, et al. "A Method for Synthesis of an Artificial Ribonuclease" Nucleosides, Nucleotides & Nucleic Acids (2001), 20(4-7):1385-88.

\* cited by examiner

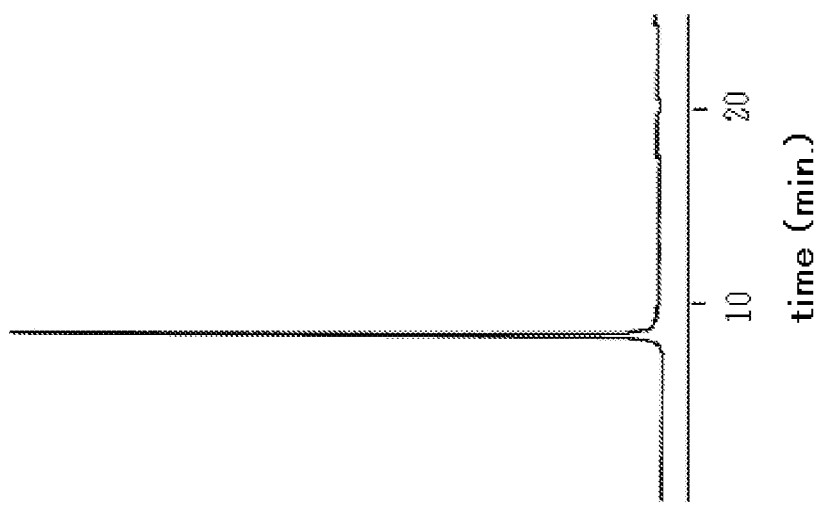

PHOSPHORAMIDITE COMPOUND AND METHOD FOR PRODUCING OLIGO-RNA

CROSS-REFERENCE TO PRIOR APPLICATIONS

This is a U.S. National Phase Application under 35 U.S.C. §371 of International Patent Application No. PCT/JP2005/015420 filed Aug. 25, 2005, and claims the benefit of Japanese Patent Application No. 2004-246185 filed Aug. 26, 2004; Japanese Patent Application No. 2005-110817 filed Apr. 7, 2005; and Japanese Patent Application No. 2005-193313 filed Jul. 1, 2005, each of which is hereby incorporated by reference in its entirety. The International Application was published in Japanese on Mar. 2, 2006 as WO 2006/022323 A1 under PCT Article 21 (2).

TECHNICAL FIELD

The present invention relates to a novel phosphoramidite compound in which a novel protecting group is introduced to the 2'-hydroxyl group, and an agent for introducing the protecting group.

BACKGROUND OF THE INVENTION

Oligoribonucleic acids (oligo-RNAs) are useful as RNA probes for gene analysis, RNA pharmaceutical materials (antisense RNA, ribozymes, RNA for RNAi-mediated control of gene expression), artificial enzymes, and aptamers. A solid synthesis method of preparing oligo-RNAs was established in the late 1980's. In the first report of the method, phosphoramidite compounds with tert-butyldimethylsilyl (TBDMS) or triisopropylsilyl (TIPS) as a 2'-hydroxyl protecting group were used (N. A. Usman et al., Journal of the American Chemical Society, Vol. 109, 7845 (1987)).

The chemical synthesis of oligo-RNAs presents many more problems than the chemical synthesis of oligodeoxyribonucleic acids (oligo-DNAs) made up of deoxyribonucleotides only.

For example, the use of the TBDMS group as a 2'-hydroxyl-protecting group may cause a side reaction in which the TBDMS group protecting the 2'-hydroxyl group migrates to the 3'-hydroxyl group during phosphoramidition of the 3'-hydroxyl group.

In addition, the use of a bulky substituent such as the TBDMS group as a 2'-hydroxyl protecting group may decrease the rate of the condensation reaction for the formation of the internucleotide bond because of steric hindrance in the vicinity of the phosphorus atom at the 3'-position, possibly resulting in cleavage or rearrangement of the internucleotide linkage during removal of the 2'-hydroxyl protecting group after oligomerization.

In order to overcome the above problems, more-efficient methods for synthesizing oligo-RNAs are now under investigation.

As a 2'-hydroxyl protecting group, the 1-(2-cyanoethoxy)ethyl (CEE) group is known to be removed together with the 3'- and 5'-protecting bissilyl group under neutral conditions capable of removing the bissilyl protecting group (Wolfgang Pfleiderer et al., Helvetica Chimica Acta, Vol. 81, 1545 (1998)).

Based on this information, Wada developed a phosphoramidite compound for producing oligo-RNAs in which the CEE group, which is capable of being removed under neutral conditions, is introduced to the 2'-hydroxy group (Takeshi Wada, Bioindustry, Vol. 21, No. 1, 17 (2004) and T. Umemoto et al., Tetrahedron Letters, Vol. 45, 9529 (2004)).

However, since the introduction of the CEE group at the 2'-hydroxyl position leads to the formation of a new asymmetric center, oligo-RNAs in which the 2'-hydroxyl groups are protected by the CEE group are a diastereoisomeric mixture. Therefore, purification and isolation of the desired oligo-RNA is complicated. In addition, since the oligo-RNAs to which the CEE group has been introduced have a methyl group on the carbon attached to the 2'-oxygen atom, some steric hindrance around the phosphorus atom attached to the 3'-hydroxyl group is expected, raising concerns about a reduction in the condensation efficiency and the condensation reaction rate.

DISCLOSURE OF THE INVENTION

Problem to be Solved by the Invention

A main object of the present invention is to provide a useful and novel phosphoramidite compound for use in a simple and high-yield method for synthesizing oligo-RNAs.

Another object of the present invention is to provide a novel ether compound which can be used to couple a protecting group to the 2'-hydroxyl group of ribose, wherein the protecting group can be removed under neutral conditions.

Means to Solve the Problems

After intensive and diligent studies, the present inventors found a compound which could accomplish the above objectives, and thus completed the present invention.

I. A Phosphoramidite Compound of the Present Invention

The present invention can include a phosphoramidite compound represented by general formula (1) (hereinafter referred to as "phosphoramidite compound of the present invention").

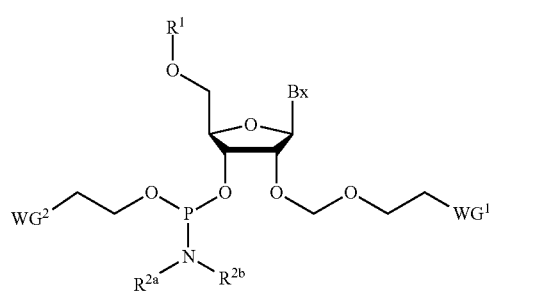

(1)

Wherein:
$B_X$ represents a nucleobase optionally having a protecting group;
$R^1$ is a substituent represented by general formula (2),

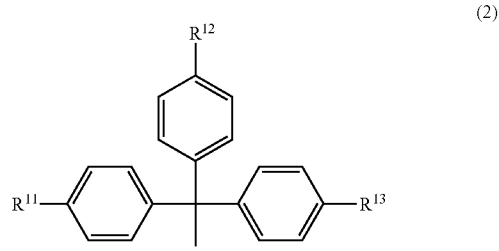

(2)

$R^{11}$, $R^{12}$ and $R^{13}$ are the same or different and each represents hydrogen or alkoxy.

$R^{2a}$ and $R^{2b}$ are the same or different and each represents alkyl, or $R^{2a}$ and $R^{2b}$, together with the adjacent nitrogen atom, may form a 5- to 6-membered saturated amino cyclic group, the amino cyclic group optionally having an oxygen or sulfur atom as a ring-composing member in addition to the adjacent nitrogen atom; and $WG^1$ and $WG^2$ are the same or different and each represents an electron-withdrawing group.

Examples of the "nucleobase" $B_X$ are not particularly limited insofar as it is a nucleobase used in the synthesis of a nucleic acid, and may include, for example, adenine, guanine, cytosine, uracil or a modified form thereof.

A "modified form" of a nucleobase means a compound in which a nucleobase bears one or more arbitrary substituents.

Examples of the "substituent" for the "modified form" of $B_X$ may include halogen, acyl, alkyl, arylalkyl, alkoxy, alkoxyalkyl, hydroxy, amino, monoalkylamino, dialkylamino, carboxy, cyano and nitro. The modified form of $B_X$ may be substituted by 1 to 3 of these substituents.

The nucleobase $B_X$ may be protected. Particularly, it is preferable that the amino group of a nucleobase having an amino group, such as adenine, guanine and cytosine, be protected.

The protecting group of the amino group is not particularly limited insofar as it is a protecting group used as a protecting group of a nucleic acid, and may include, for example, benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene.

Examples of the "saturated amino cyclic group" of $R^2$ may include pyrrolidine-1-yl, piperidine-1-yl, morpholine-1-yl and thiomorpholine-1-yl.

The electron-withdrawing groups $WG^1$ and $WG^2$ may include cyano, nitro, alkylsulfonyl and halogen. Among them, cyano is preferable.

Examples of the "halogen" of the phosphoramidite compound of the present invention may include fluorine, chlorine, bromine and iodine.

Examples of the "acyl" of the phosphoramidite compound of the present invention may include a straight or branched alkanoyl having 1 to 6 carbon atoms and aroyl having 7 to 13 carbon atoms. Specifically, the acyl may include, for example, formyl, acetyl, n-propionyl, isopropionyl, n-butyryl, isobutyryl, tert-butyryl, valeryl, hexanoyl, benzoyl, naphthoyl and levulinyl.

Examples of the "alkyl" of the phosphoramidite compound of the present invention may include a straight or branched alkyl having 1 to 5 carbon atoms. Specifically, the alkyl may include, for example, methyl, ethyl, n-propyl, isopropyl, n-butyl, isobutyl, sec-butyl, tert-butyl, n-pentyl, isopentyl, neopentyl and tert-pentyl. The alkyl may be substituted and examples of the "substituent" may include halogen, alkyl, alkoxy, cyano and nitro. The alkyl may be substituted by 1 to 3 of these substituents.

Examples of the "alkyl" moiety of the "arylalkyl", "alkoxyalkyl", "monoalkylamino", "dialkylamino" and "alkylsulfonyl" of the phosphoramidite compound of the present invention may include the same alkyl groups mentioned above.

Examples of the "alkoxy" of the phosphoramidite compound of the present invention may include a straight or branched alkoxy having 1 to 4 carbon atoms.

Specifically, the alkoxy may include, for example, methoxy, ethoxy, n-propoxy, isopropoxy, n-butoxy, isobutoxy, sec-butoxy and tert-butoxy. Among these, alkoxy groups having 1 to 3 carbon atoms are preferable, and methoxy is more preferable.

Examples of the "alkoxy" moiety of the "alkoxyalkyl" of the phosphoramidite compound of the present invention may include the same alkoxy groups mentioned above.

Examples of the "aryl" moiety of the "arylalkyl" of the phosphoramidite compound of the present invention may include aryl groups having 6 to 12 carbon atoms. Specifically, the aryl may include, for example, phenyl, 1-naphthyl, 2-naphthyl and biphenyl. The aryl may be substituted, and examples of the "substituent" may include halogen, alkyl, alkoxy, cyano and nitro. The aryl may be substituted with 1 to 3 of these substituents. Examples of the "halogen", "alkyl" and "alkoxy", which are substituents of the alkyl or aryl of the phosphoramidite compound of the present invention, may include, respectively, the same groups mentioned above.

The phosphoramidite compound of the present invention can be used as a reagent for producing oligo-RNAs. The phosphoramidite compound of the present invention is a phosphoramidite compound having an ether-type protecting group at the 2'-hydroxyl position, which can be removed under neutral conditions. In addition, the phosphoramidite compound of the present invention is characterized by the fact that the condensation reaction proceeds in a shorter time and results in a better yield during the synthesis of oligo-RNAs when compared with a conventional phosphoramidite compound. This is because the ether-type protecting group introduced to the 2'-hydroxyl group is a linear protecting group and therefore does not sterically crowd the space around the phosphorus atom attached to the 3'-hydroxyl group. The phosphoramidite compound of the present invention makes it possible to produce oligo-RNAs of high purity by essentially the same method used in the production of oligo-DNAs.

In the present document, the term "oligo-DNA" means an oligonucleic acid having deoxyribonucleotides only. In addition, in the present document, the term "oligo-RNA" means an oligonucleic acid containing at least one ribonucleotide and which may also have one or more deoxyribonucleotides.

Specific examples of the phosphoramidite compound of the present invention may include the following compounds 1 to 5:

1. $N^6$-acetyl-5'-O-(4,4'-dimethoxytrityl)-2'-O-(2-cyanoethoxymethyl)adenosine 3'-O-(2-cyanoethyl N,N-diisopropylphosphoramidite)
2. $N^2$-acetyl-5'-O-(4,4'-dimethoxytrityl)-2'-O-(2-cyanoethoxymethyl)guanosine 3'-O-(2-cyanoethyl N,N-diisopropylphosphoramidite)
3. $N^2$-phenoxyacetyl-5'-O-(4,4'-dimethoxytrityl)-2'-O-(2-cyanoethoxymethyl)guanosine 3'-O-(2-cyanoethyl N,N-diisopropylphosphoramidite)
4. $N^4$-acetyl-5'-O-(4,4'-dimethoxytrityl)-2'-O-(2-cyanoethoxymethyl)cytidine 3'-O-(2-cyanoethyl N,N-diisopropylphosphoramidite)
5. 5'-O-(4,4'-dimethoxytrityl)-2'-O-(2-cyanoethoxymethyl)uridine 3'-O-(2-cyanoethyl N,N-diisopropylphosphoramidite)

BRIEF DESCRIPTION OF THE DRAWINGS

FIG. 1 shows a chromatogram obtained by reverse-phase HPLC analysis of the objective compound of Example 16. In the FIGURE, the horizontal axis indicates the time (minutes), and the vertical axis indicates the optical absorbance.

BEST MODE FOR CARRYING OUT THE INVENTION

II. Method of Producing the Phosphoramidite Compound of the Present Invention The phosphoramidite compound of the present invention can be produced as follows.

In the following production method, it is common, when raw materials have a substituent that affects the reaction (e.g., hydroxyl, amino and carboxy), for the raw materials to be used for reaction after being protected with a suitable protecting group according to a known method.

After the reaction is completed, the protecting group can be removed by a known method such as catalytic reduction, alkali treatment, acid treatment or the like. The phosphoramidite compound of the present invention can be produced from a known compound or an intermediate which can easily be produced through the following steps a to h, for example.

The method of producing the phosphoramidite compound of the present invention is described in detail below.

(1) Step a:

Producing a nucleoside derivative represented by general formulas (15) and (15'), wherein an ether-type protecting group which can be removed under neutral conditions is introduced to the 2'-hydroxyl group by allowing an alkylating reagent to act on a nucleoside derivative represented by general formula (14).

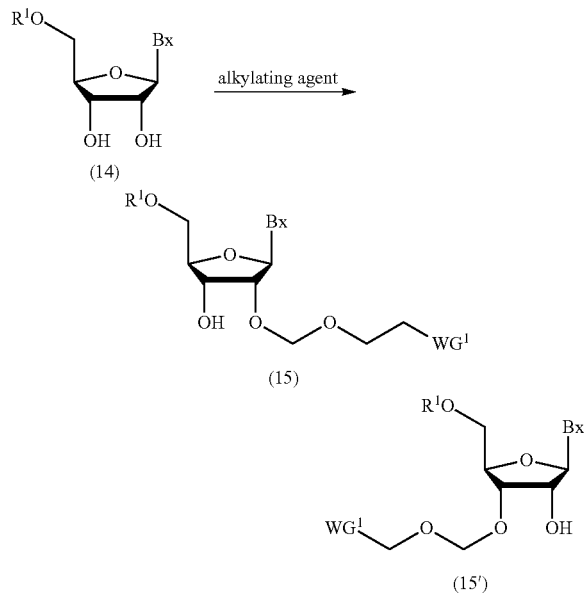

Wherein:
$B_X$, $R^1$ and $WG^1$ are the same as defined above.

Examples of the "alkylating reagent" may include an ether compound represented by general formula (13).

Wherein:
L represents halogen, an arylthio group, an alkyl sulfoxide group or an alkylthio group; and $WG^1$ is the same as defined above.

Examples of the "halogen", the "aryl" moiety of the "arylthio group", and the "alkyl" moieties of the "alkylsulfoxide group" and the "alkylthio group" of L may include the same halogen, aryl and alkyl, respectively, as those of the phosphoramidite compound of the present invention.

Specific examples of the ether compound (13) may include the following compounds 1 and 2:
1. Chloromethyl 2-cyanoethylether
2. 2-Cyanoethylmethylthiomethylether The ether compound (13) is a new alkylating reagent which can introduce an ether-type substituent, which is removable under neutral conditions, to the 2'-hydroxyl position under basic conditions, and which is useful as a reagent for producing the phosphoramidite compound of the present invention.

The ether compound (13) can be produced by the following steps 1 to 4.

Step 1:

Producing a compound represented by general formula (24) by alkylthiomethylating an alcohol compound represented by general formula (20).

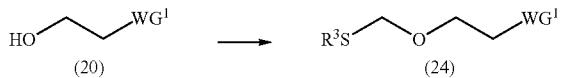

Wherein:
$WG^1$ is the same as defined above; and
$R^3$ represents alkyl or aryl.

The compound (24) is the ether compound (13) wherein L is an alkylthio group.

Examples of the "alkyl" of $R^3$ may include the same alkyl as that of the phosphoramidite compound of the present invention.

When $R^3$ is methyl, examples of the "alkylthiomethylating reagent" may include a mixed solvent containing dimethylsulfoxide, acetic anhydride and acetic acid. The amount of dimethylsulfoxide to be used may be in the range of 10 to 200 mol per mol of compound (20), and preferably 20 to 100 mol per mol of compound. The amount of acetic acid to be used may be in the range of 10 to 150 mol per mol of compound (20), and preferably 20 to 100 mol per mol of compound. The amount of acetic anhydride to be used may be in the range of 10 to 150 mol per mol of compound (20), and preferably 20 to 100 mol per mol of compound. The reaction temperature is preferably in the range of 0° C. to 100° C. The reaction time varies depending on the kind of raw materials and the reaction temperature, and is preferably between 1 and 48 hours.

Step 2:

Producing a compound represented by general formula (25) by halogenating compound (24).

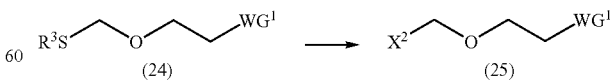

Wherein:
$WG^1$ and $R^3$ are the same as defined above; and
$X^2$ represents the halogen.

Compound (25) is a compound wherein L of the ether compound (13) is a halogen.

Examples of the "halogen" $X^2$ may include the same halogen as that of the phosphoramidite compound of the present invention.

The step can be carried out by a known method (e.g., T. Benneche et al., Synthesis 762 (1983)).

The solvent to be used is not specifically limited unless it is involved in the reaction, and may include, for example, a halogenated hydrocarbon such as dichloromethane, chloroform, carbon tetrachloride and 1,2-dichloroethane.

Examples of the "halogenating agent" may include sulfuryl chloride and phosphorus oxychloride.

The amount of the halogenating agent to be used may suitably be in the range of 1 to 20 mol per mol of compound (24), and preferably 1 to 10 mol per mol of the compound. The reaction temperature is preferably in the range of 0° C. to 100° C. The reaction time varies depending on the kind of raw materials and the reaction temperature, and is preferably between 30 minutes and 24 hours.

Step 3:

Producing a compound represented by general formula (25a) by arylthiolating the compound (25).

Wherein:

$WG^1$ and $X^2$ are the same as defined above; and $R^{3a}$ represents aryl.

Compound (25a) is a compound of the class of ether compounds (13) wherein L is an arylthio group. Examples of the "aryl" $R^{3a}$ may include the same aryl as that of the phosphoramidite compound of the present invention. The step can be carried out by a known method. The solvent to be used is not specifically limited unless it is involved in the reaction, and may include, for example, dichloromethane and acetonitrile. Examples of the "arylthiolating reagent" may include thiophenol and 4-methyl benzenethiol. The amount of the arylthiolating reagent to be used may be in the range of 1 to 20 mol per mol of compound (25), and preferably 1 to 5 mol per mol of the compound. The reaction temperature is preferably in the range of 0° C. to 100° C. The reaction time varies depending on the kind of raw materials and the reaction temperature, and is preferably between 1 and 48 hours.

Step 4:

Producing a compound represented by general formula (24a) by oxidizing the compound (24).

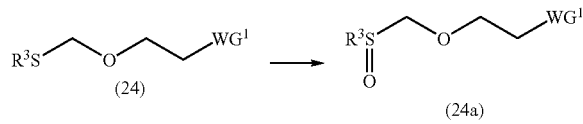

Wherein:

$WG^1$ and $R^3$ are the same as defined above.

The compound (24a) is a compound of the class of ether compounds (13) wherein L is an alkyl sulfoxide group. Examples of the "alkyl" $R^3$ may include the same alkyl as that of the phosphoramidite compound of the present invention.

The step can be carried out by a known method.

The solvent to be used is not specifically limited unless it is involved in the reaction, and may include, for example, dichloromethane, chloroform and methanol. Examples of the "oxidizing agent" may include metachloroperbenzoic acid, metaperiodate salt and hydrogen peroxide. The amount of the oxidizing agent to be used may be in the range of 1 to 10 mol per mol of compound (24), and preferably 1 to 2 mol per mol of the compound. The reaction temperature is preferably in the range of 0° C. to 100° C. The reaction time varies depending on the kind of raw materials and the reaction temperature, and is preferably between 1 and 48 hours. When compound (25) is used as the alkylating reagent, the step can be performed as follows.

The step can be performed by reacting the alkylating reagent and a base with compound (14), which is commercially available or is synthesized according to a known method.

The solvent to be used is not specifically limited unless it is involved in the reaction, and may include, for example, a halogenated hydrocarbon such as dichloromethane, chloroform, carbon tetrachloride and 1,2-dichloroethane. The amount of the alkylating reagent to be used may be in the range of 1 to 20 mol per mol of compound (14), and preferably 1 to 10 mol per mol of the compound. In the step, by way of the intermediate produced by reacting a metal reagent and a base with compound (14), the alkylating reagent may be reacted if necessary. Examples of the "metal reagent" may include dibutylstannyl dichloride. The amount of the metal reagent to be used may be in the range of 1 to 20 mol per mol of compound (14), and preferably 1 to 10 mol per mol of the compound. Examples of the "base" may include an organic base such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may be in the range of 1 to 20 mol per mol of compound (14), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

When compound (24) or (25a) is used as the alkylating reagent, the step can be performed as follows.

The step can be performed by reacting the alkylating reagent, an acid and a reagent for halogenating the sulfur atom on compound (14) which is commercially available or is synthesized according to a known method (e.g., M. Matteucci, Tetrahedron Letters, Vol. 31, 2385 (1990)). The amount of the alkylating reagent to be used may be in the range of 1 to 5 mol per mol of compound (14), and preferably 1.05 to 3 mol per mol of the compound. Examples of the "acid" may include trifluoromethanesulfonic acid, silver trifluoromethanesulfonate and trimethylsilyl trifluoromethanesulfonate. The amount of the acid to be used may be in the range of 0.01 to 20 mol per mol of compound (14), and preferably 0.02 to 10 mol per mol of the compound. The solvent to be used is not specifically limited unless it is involved in the reaction, and may include, for example, dichloromethane, chloroform, carbon tetrachloride, 1,2-dichloroethane, benzene, toluene, xylene, tetrahydrofuran, acetonitrile and mixtures thereof. Examples of the "reagent for halogenating a sulfur atom" to be used in the step may include N-bromosuccinimide (NBS) and N-iodosuccinimide (NIS). The amount of the reagent for halogenating a sulfur atom to be used may be in the range of 1 to 10 mol per mol of compound (14), and preferably 1.05 to 5 mol per mol of the compound. The reaction temperature is preferably in the range of −78° C. to 30° C. The reaction time varies depending on the kind of raw materials and the reaction temperature, and is preferably between 5 minutes and 5 hours.

When the compound (24a) is used as the alkylating reagent, the step can be performed as follows.

The step can be performed by reacting the alkylating reagent, an acid anhydride and a base with compound (14) which is commercially available or is synthesized according to a known method. The amount of the alkylating reagent to be used may be in the range of 1 to 5 mol per mol of compound (14), and preferably 1.05 to 3 mol per mol of the compound. Examples of the "acid anhydride" may include trifluoromethanesulfonic anhydride and acetic anhydride. The amount of the acid anhydride to be used may be in the range of 0.01 to 20 mol per mol of compound (14), and preferably 0.02 to 10 mol per mol of the compound. Examples of the "base" may include tetramethylurea and collidine. The amount of the base to be used may be in the range of 0.01 to 20 mol per mol of compound (14), and preferably 0.02 to 10 mol per mol of the compound. The solvent to be used is not specifically limited unless it is involved in the reaction, and may include, for example, dichloromethane, chloroform, carbon tetrachloride, 1,2-dichloroethane and mixtures thereof. The reaction temperature is preferably in the range of −78° C. to 30° C. The reaction time varies depending on the kind of the materials and the reaction temperature, and is preferably between 5 minutes and 24 hours.

(2) Step b:

Isolating and purifying the nucleoside derivative (15) produced by step (a);

In the step, the nucleoside derivative can be isolated and purified from the mixture produced by step (a) by using a standard separation and purification technique such as thin-layer chromatography, silica gel column chromatography or the like.

(3) Step c:

Separately from step b, for producing a ribonucleic acid compound represented by general formula (17), wherein an ether-type protecting group which can be removed under neutral conditions is introduced to the 2'-hydroxyl group, by allowing an alkylating reagent to act on a ribonucleic acid compound represented by general formula (16).

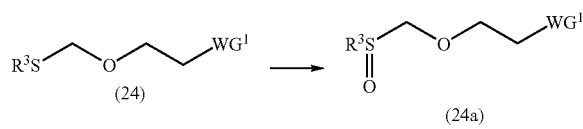

Wherein:

$B_X$ and $WG^1$ are the same as defined above; and

A represents a silicon substituent represented by general formula (18a) or (18b).

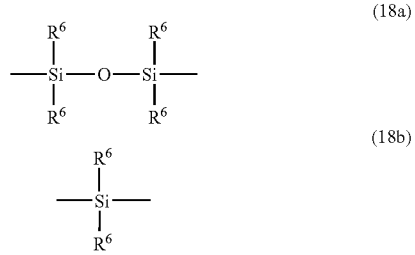

Wherein:

$R^6$ represents alkyl.

Examples of the "alkyl" of $R^6$ may include the same alkyl as that of the phosphoramidite compound of the present invention.

Examples of the "alkylating reagent" may include the same items as mentioned above.

When the compound (25) is used as the alkylating reagent, the step can be performed as follows.

The step can be performed by reacting the alkylating reagent and a base with compound (16), which is commercially available or is synthesized according to a known method.

The solvent to be used is not specifically limited unless it is involved in the reaction, and may include, for example, a halogenated hydrocarbon such as dichloromethane, chloroform, carbon tetrachloride and 1,2-dichloroethane. The amount of the alkylating reagent to be used may be in the range 1 to 20 mol per mol of compound (14), and preferably 1 to 10 mol per mol of the compound. In the step, after going by way of the intermediate produced by reacting a metal reagent and a base with compound (16), the alkylating reagent may be reacted if necessary. Examples of the "metal reagent" may include dibutylstannyl dichloride and t-butyl magnesium chloride. The amount of the metal reagent to be used may be in the range of 1 to 20 mol per mol of compound (16), and preferably 1 to 10 mol per mol of the compound. Examples of the "base" may include an organic base such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may in the range of 1 to 20 mol per mol of compound (16), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

When the compound (24) or (25a) is used as the alkylating reagent, the step can be performed as follows.

The step can be performed by reacting the alkylating reagent, an acid and a reagent for halogenating the sulfur atom of compound (16), which is commercially available or is synthesized according to a known method (for example, M. Matteucci, Tetrahedron Letters, Vol. 31, 2385 (1990)). The amount of the alkylating reagent to be used may be in the range of 1 to 5 mol per mol of compound (16), and preferably 1.05 to 3 mol per mol of the compound. Examples of the "acid" may include trifluoromethanesulfonic acid, silver trifluoromethanesulfonate and trimethylsilyl trifluoromethanesulfonate. The amount of the acid to be used may be in the range of 0.01 to 20 mol per mol of compound (16), and preferably 0.02 to 10 mol per mol of the compound. The solvent to be used is not specifically limited unless it is involved in the reaction, and may include, for example, dichloromethane, chloroform, carbon tetrachloride, 1,2-dichloroethane, benzene, toluene, xylene, tetrahydrofuran, acetonitrile and mixtures thereof. Examples of the "reagent for halogenating a sulfur atom" to be used in the step may include N-bromosuccinimide (NBS), N-iodosuccinimide (NIS). The amount of the reagent for halogenating a sulfur atom to be used may be in the range of 1 to 10 mol per mol of compound (16), and preferably 1.05 to 5 mol per mol of the compound. The reaction temperature is preferably in the range of −78° C. to 30° C. The reaction time varies depending on the kind of raw materials and the reaction temperature, and is preferably between 5 minutes and 5 hours.

When the compound (24a) is used as the alkylating reagent, the step can be performed as follows.

The step can be performed by reacting the alkylating reagent, an acid anhydride and a base with compound (16) which is commercially available or is synthesized according to a known method. The amount of the alkylating reagent to be used may be in the range of 1 to 5 mol per mol of compound (16), and preferably 1.05 to 3-mol per mol of the compound. Examples of the "acid anhydride" may include trifluoromethanesulfonic anhydride and acetic anhydride. The amount of the acid anhydride to be used may be in the range of 0.01 to 20 mol per mol of compound (16), and preferably 0.02 to 10 mol per mol of the compound. Examples of the "base" may include tetramethylurea and collidine. The amount of the base to be used may be in the range of 0.01 to 20 mol per mol of compound (16), and preferably 0.02 to 10 mol per mol of the compound. The solvent to be used is not specifically limited unless it is involved in the reaction, and may include, for example, dichloromethane, chloroform, carbon tetrachloride, 1,2-dichloroethane and mixtures thereof. The reaction temperature is preferably in the range of −78° C. to 30° C. The reaction time varies depending on the kind of raw materials and the reaction temperature, and is preferably between 5 minutes and 24 hours.

(4) Step d:

Separately from steps a to c, for producing a ribonucleic acid compound represented by general formula (19) by allowing dimethylsulfoxide, acetic acid and acetic anhydride to act on the ribonucleic acid compound (16).

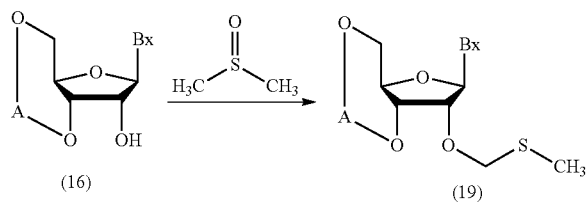

Wherein:

A and $B_X$ are the same as defined above.

The step can be performed by reacting dimethylsulfoxide, acetic acid and acetic anhydride with compound (14), which is commercially available or is synthesized according to a known method.

The step can be performed by reacting dimethylsulfoxide, acetic acid and acetic anhydride with compound (14), which is commercially available or is synthesized according to a known method.

The amount of dimethylsulfoxide to be used may be in the range of 10 to 200 mol per mol of compound (16), and preferably from 20- to 100-fold mol per mol of the compound.

The amount of acetic acid to be used may be in the range of 10 to 150 mol per mol of compound (16), and preferably 20 to 100 mol per mol of the compound. The amount of acetic anhydride to be used may be in the range of 10 to 150 mol per mol of compound (16), and preferably 20 to 100 mol per mol of the compound. The reaction temperature is preferably in the range of 10° C. to 50° C. The reaction time varies depending on the kind of raw materials and the reaction temperature, and is preferably between 30 minutes and 24 hours.

(5) Step e:

Producing a ribonucleic acid compound represented by general formula (17), wherein an ether-type protecting group which can be removed under neutral conditions is introduced to the 2'-hydroxyl group, by allowing an alcohol compound represented by general formula (20), an acid and a reagent for halogenating a sulfur atom to act on a nucleoside derivative (19) produced by step d.

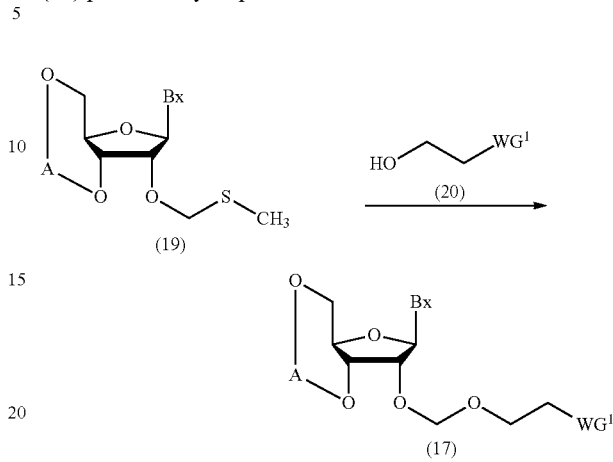

Wherein:

A, $B_X$ and $WG^1$ are the same as defined above.

The step can be performed by reacting the alcohol compound (20), an acid and a reagent for halogenating the sulfur atom on the ribonucleic acid compound (19) according to a known method. The solvent to be used is not specifically limited unless it is involved in the reaction, and may include, for example, dichloromethane, chloroform, carbon tetrachloride, 1,2-dichloroethane, benzene, toluene, xylene, tetrahydrofuran, acetonitrile and mixtures thereof. The amount of the alcohol compound (20) to be used may be in the range of 1 to 20 mol per mol of compound (19), and preferably 1 to 10 mol per mol of the compound. Examples of the "acid" may include trifluoromethanesulfonic acid, silver trifluoromethanesulfonate and trimethylsilyl trifluoromethanesulfonate. Examples of the "reagent for halogenating a sulfur atom" may include N-bromosuccinimide (NBS), N-iodosuccinimide (NIS). The amount of the reagent for halogenating a sulfur atom to be used may be in the range of 0.1 to 20 mol per mol of compound (19), and preferably 0.2 to 10 mol per mol of the compound. The reaction temperature is preferably in the range of −100° C. to 20° C. The reaction time varies depending on the kind of raw materials and the reaction temperature, and is preferably between 5 minutes and 12 hours.

(6) Step f:

Producing a ribonucleic acid compound represented by general formula (21) by removing the protecting groups of the 3'- and 5'-hydroxyl groups of the ribonucleic acid compound (17) produced by step c or step e.

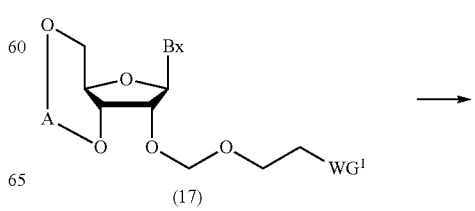

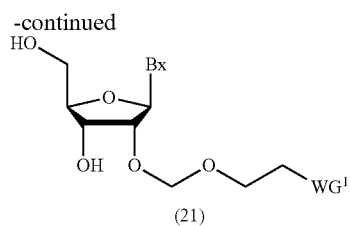

(21)

Wherein:

A, $B_X$ and $WG^1$ are the same as defined above.

The step can be performed by dissolving the compound (17) in an organic solvent, and reacting a fluorinating agent and an acid as a mixture of an arbitrary mixing ratio. Examples of the "fluorinating agent" to be used in the step may include ammonium fluoride, tetra n-butylammonium fluoride (TBAF), triethylamine trihydrofluoride, hydrogen fluoride pyridine. The amount of the fluorinating agent to be used may be in the range of 0.1 to 20 mol per mol of compound (17), and preferably 0.2 to 10 mol per mol of the compound. The reaction temperature is preferably in the range of 0° C. to 120° C. The reaction time varies depending on the kind of raw materials and the reaction temperature, and is preferably between 30 minutes and 24 hours.

(7) Step g:

Producing a ribonucleic acid compound (15) by introducing a protecting group ($R^1$), which can be removed under acidic conditions, into the 5'-hydroxyl group of the ribonucleic acid compound (21) produced by step f.

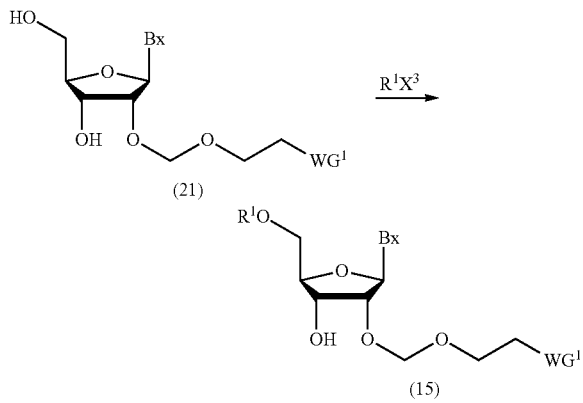

Wherein:

A, $B_X$, $R^1$ and $WG^1$ are the same as defined above; and $X^3$ represents halogen.

Examples of the "halogen" of $X^3$ may include the same halogen as those of the phosphoramidite compound of the present invention. The step can be performed by reacting $R^1X^3$ with compound (21) according to a known method. The amount of $R^1X^3$ to be used may be in the range of 1 to 20 mol per mol of compound (21), and preferably 1 to 10 mol per mol of the compound. The solvent to be used is not specifically limited unless it is involved in the reaction, and may include, for example, acetonitrile and tetrahydrofuran. Examples of the "base" may include an organic base such as pyridine, 2,6-dimethylpyridine, 2,4,6-trimethylpyridine, N-methylimidazole, triethylamine, tributylamine, N,N-diisopropylethylamine and 1,8-diazabicyclo[5.4.0]-7-undecene. The amount of the base to be used may be in the range of 1 to 20 mol per mol of compound (21), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours.

(8) Step h:

Producing the phosphoramidite compound of the present invention by phosphoramiditing the 3'-hydroxyl group by allowing a phosphoramiditing reagent and if necessary an activating agent to act on a nucleoside derivative (15) produced by step b or step f.

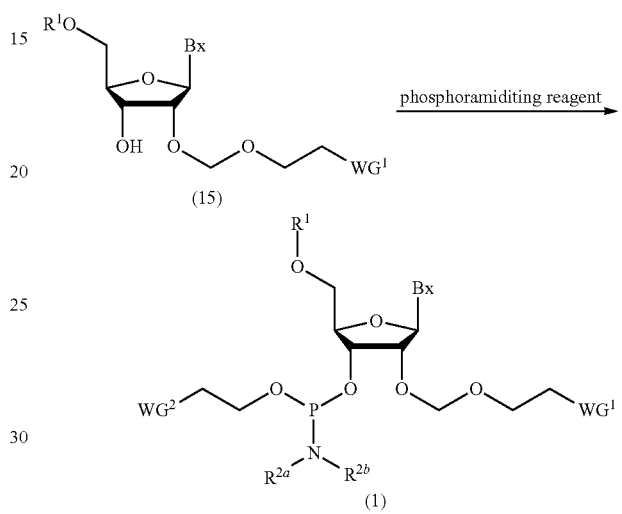

Wherein:

$B_X$, $R^1$, $R^{2a}$, $R^{2b}$, $WG^1$ and $WG^2$ are the same as defined above.

Examples of "the phosphoramiditing reagent" may include the compound represented by general formula (22) and (23).

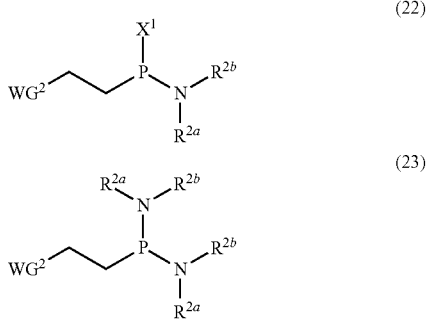

Wherein:

$R^{2a}$, $R^{2b}$ and $WG^2$ are the same as defined above; and $X^1$ represents halogen.

Examples of the "halogen" of $X^1$ may include the same halogen as those of the phosphoramidite compound of the present invention. The step is a reaction for phosphoramiditing the 3'-hydroxyl group by reacting the phosphoramiditing reagent with compound (15), and can be performed according to a known method. An activating agent can be used if necessary. The solvent to be used is not specifically limited unless it is involved in the reaction, and may include, for example, acetonitrile and tetrahydrofuran.

The amount of the phosphoramiditing reagent to be used may be in the range of 1 to 20 mol per mol of compound (15), and preferably 1 to 10 mol per mol of the compound. Examples of the "activating agent" may include 1H-tetrazole, 5-ethylthiotetrazole, 4,5-dichloroimidazole, 4,5-dicyanoimidazole, benzotriazole triflate, imidazole triflate, pyridinium triflate, N,N-diisopropylethylamine and 2,4,6-collidine/N-methylimidazole. The amount of the activating agent to be used may be in the range of 1 to 20 mol per mol of compound (15), and preferably 1 to 10 mol per mol of the compound. The reaction temperature is preferably in the range of 0° C. to 120° C. The reaction time varies depending on the kind of raw materials and the reaction temperature, and is preferably between 30 minutes and 24 hours. The phosphoramidite compound of the present invention thus produced can be isolated and purified by a method known per se, such as concentration, liquid phase conversion, partition, solvent extraction, crystallization, recrystallization, fractional distillation or chromatography.

III. Method for Producing Oligo-RNAs

The present invention may include a method for producing oligo-RNAs represented by general formula (3), the method comprising using the phosphoramidite compound of the present invention.

The details are described below.

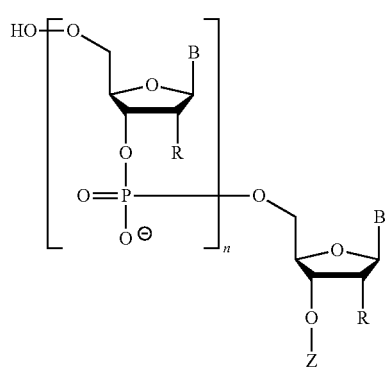

(3)

Wherein:
each B represents independently adenine, guanine, cytosine, uracil, thymine or a modified form thereof;
each R represents independently H or hydroxyl, and at least one of the R groups is hydroxyl;
Z represents H or a phosphate group; and
n represents an integer between 1 and 100.

n is preferably an integer between 10 and 50, and more preferably an integer between 15 and 30.

Examples of the "substituent" for the "modified form" of B may include halogen, acyl, alkyl, arylalkyl, alkoxy, hydroxyl, amino, monoalkylamino, dialkylamino, carboxy, cyano and nitro; and the modified form of B may be substituted with 1 to 3 of these substituents.

Examples of the "halogen", "aryl", "alkyl", "arylalkyl", "alkoxy", "alkoxyalkyl", "amino", "monoalkylamino" and "dialkylamino" for the "modified form" of B may include the same items as those of the phosphoramidite compound of the present invention.

A method for producing an oligo-RNA (3) with the phosphoramidite compound of the present invention can be performed by a known method and, for example, can be performed by condensing a nucleic acid monomer compound to the direction from 3' to 5' step by step according to the following steps A to G.

Compounds and reagents to be used in the following step except the phosphoramidite compound of the present invention are not particularly limited insofar as they are generally used in synthesis of oligo-RNAs or oligo-DNAs. In addition, all the steps can be performed by using an automatic synthesizer for DNA or in manual as in the case of using conventional agents for synthesizing a nucleic acid. The use of an automated synthesizer is desirable from the point of view of the simplicity and ease of the method and the accuracy of the synthesis. Compounds and reagents described in the following steps A to G except a nucleic acid monomer compound are not particularly limited insofar as they are generally used in synthesis of oligo-DNAs or oligo-RNAs.

(1) Step A:

Producing a compound represented by general formula (5) by removing the 5'-hydroxyl group from a compound represented by general formula (4) by reacting an acid.

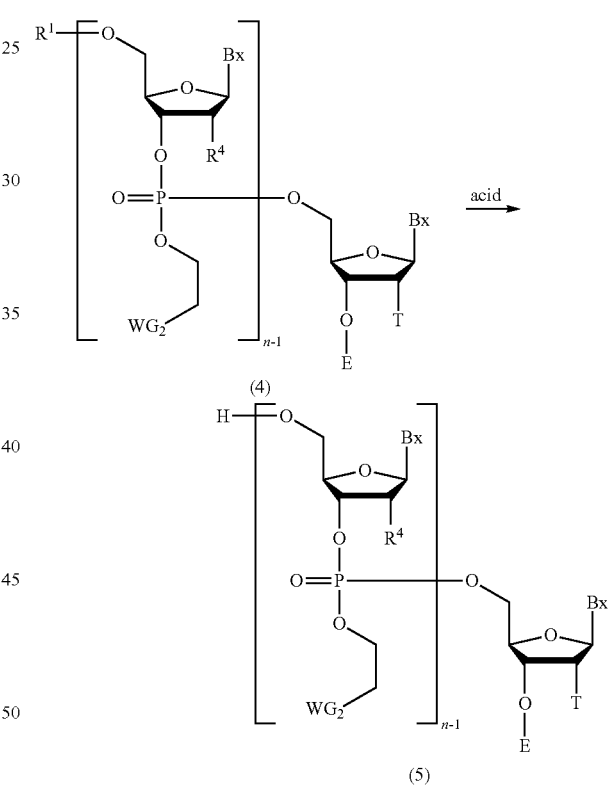

Wherein:
n, $R^1$ and $WG^2$ are the same as defined above;
each B represents independently adenine, guanine, cytosine, uracil, thymine or a modified form thereof; and each $R^4$ represents independently H, acyloxy or a substituent represented by general formula (6).

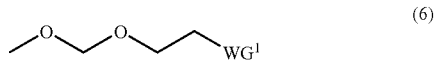

(6)

Wherein:

WG$^1$ is the same as defined above; and

E represents acyl or a substituent represented by general formula (7).

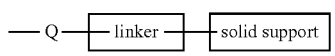
(7)

Wherein:

Q represents single bond or a substituent represented by general formula (8).

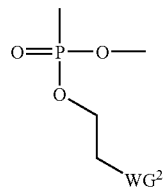
(8)

Wherein:

WG$^2$ is the same as defined above; and

T represents H, acyloxy, a substituent represented by the above general formula (6) or (7), with the proviso that either E or T is a substituent (7).

The step is performed by reacting an acid to a compound represented by general formula (26a), (26b) [a compound (4) wherein n is 1] which is attached to the solid support, or an oligo-RNA or an oligo-DNA produced by performing the operations of step A to step D [compound (4) wherein n is 2 to 100] which is attached to the solid support (hereinafter referred to as the "compound attached to the solid support").

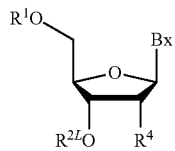
(26a)

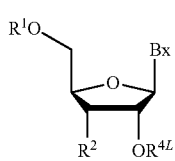
(26b)

Wherein:

B$_X$ and R$^1$ are the same as defined above;

R$^{2L}$ and R$^{4L}$ represent a substituent (7);

R$^2$ represents acyloxy; and

R$^4$ represents H, acyloxy or a substituent (6).

Examples of the "acyl" moiety of the "acyloxy" group of R$^2$ and R$^4$ may include acetyl, propionyl, butyryl, isobutyryl, benzoyl, 4-methoxybenzoyl, phenylacetyl, phenoxyacetyl, 4-tert-butylphenoxyacetyl and 4-isopropylphenoxyacetyl. Examples of the "solid support" may include a controlled-pore glass (CPG), an oxalyl-controlled pore glass (see, for example, Alul et al., Nucleic Acids Research, Vol. 19, 1527 (1991)), TentaGel support—amino polyethylene glycol derivatization support (see, for example, Wright et al., Tetrahedron Letters, Vol. 34, 3373 (1993)) and a copolymer of Poros-polystyrene and divinylbenzene. Examples of the "linker" may include 3-aminopropyl, succinyl, 2,2'-diethanol sulfonyl and a long chain alkylamino (LCAA). The compounds (26a) and (26b) are attached to the solid support, which are produced according to a known method or are commercially available, and examples of a preferable embodiment are a compound represented by general formula (27) or (28).

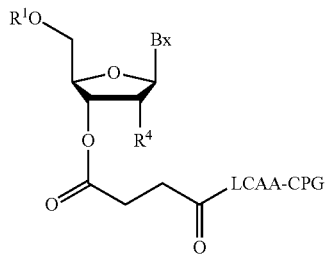
(27)

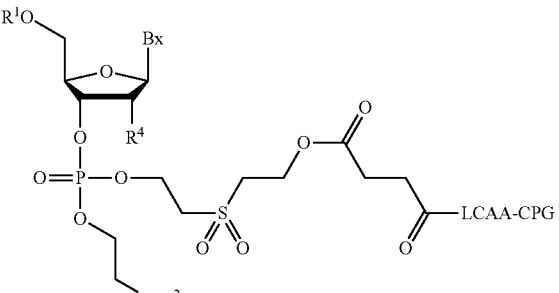
(28)

Wherein:

B$_X$, R$^1$, R$^4$ and WG$^2$ are the same as defined above.

The compounds (27) and (28) wherein R$^4$ is a substituent (6) can be produced from a phosphoramidite compound of the present invention according to a known method. Examples of the "acid" to be used in the step may include trifluoroacetic acid, dichloroacetic acid, trichloroacetic acid. The acid to be used in the step can be diluted in a suitable solvent so as to be of a concentration of 1 to 5%. The solvent is not specifically limited unless it is involved in the reaction, and may include, for example, dichloromethane, acetonitrile, water and mixtures thereof. The reaction temperature in the reaction is preferably in the range of 20° C. to 50° C. The reaction time varies depending on the kind of the acid and the reaction temperature, and is preferably between 1 minute and 1 hour.

The amount of the reagent to be used is preferably in the range of 1 to 100 mol per mol of compound attached to the solid support, and more preferably 1 to 10 mol per mol of compound attached to the solid support.

(2) Step B:

Producing a compound represented by general formula (9) by condensing a nucleic acid monomer compound with the compound produced by step A using an activating agent.

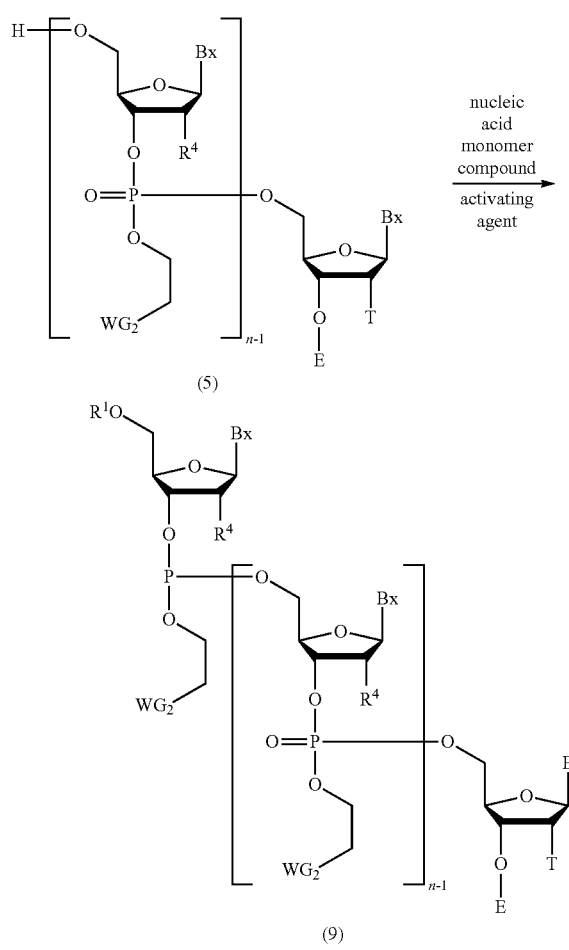

(5)

(9)

Wherein:

$B_X$, E, n, $R^1$, $R^4$, T and $WG^2$ are the same as defined above.

The step can be performed by reacting a nucleic acid monomer compound and an activating agent with a compound attached to the solid support. Examples of the "nucleic acid monomer compound" may include the phosphoramidite compound of the present invention and a compound represented by general formula (29) which is commercially available.

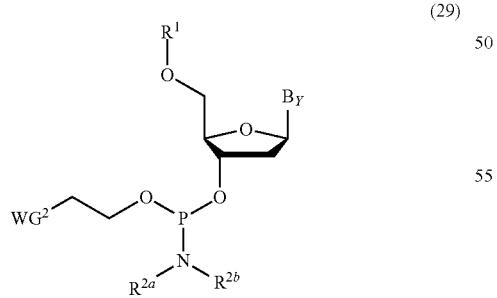

(29)

Wherein:

$R^1$, $R^{2a}$, $R^{2b}$ and $WG^2$ are the same as defined above; and $B_Y$ represents a nucleobase optionally having a protecting group.

Examples of the "nucleobase" $B_Y$ is not particularly limited insofar as it is a nucleobase used to synthesize a nucleic acid, and may include, for example, adenine, guanine, cytosine, thymine and a modified form thereof. The modified form is the same as defined above for $B_X$.

Examples of the "substituent" for the "modified form" of $B_Y$ may include halogen, alkyl, arylalkyl, alkoxy, hydroxyl, amino, monoalkylamino, dialkylamino, carboxy, cyano and nitro; and the modified form of $B_Y$ may be substituted with 1 to 3 of these substituents. Examples of the "halogen", "aryl", "alkyl", "arylalkyl", "alkoxy", "alkoxyalkyl", "amino", "monoalkylamino" and "dialkylamino" for the "modified form" of $B_Y$ may include the same items as those of the phosphoramidite compound of the present invention.

The nucleobase of $B_Y$ may be protected, and especially, the nucleobase having an amino group (for example adenine, guanine, cytosine) may preferably be protected of the amino group. The protecting group of amino group of the $B_Y$ may include the same items as those of $B_X$.

Examples of the "activating agent" may include the same items as mentioned above.

The reaction solvent is not specifically limited unless it is involved in the reaction, and may include, for example, acetonitrile and tetrahydrofuran. The reaction temperature in the reaction is preferably in the range of 20° C. to 50° C.

The reaction time varies depending on the kind of the activating agent and the reaction temperature, and is preferably between 1 minute and 1 hour. The amount of the agent to be used is preferably in the range of 1 to 100 mol per mol of compound attached to the solid support, and more preferably 1 to 10 mol per mol of compound attached to the solid support.

(3) Step C:

Capping the 5'-hydroxyl group of the unreacted compound (5) in step B.

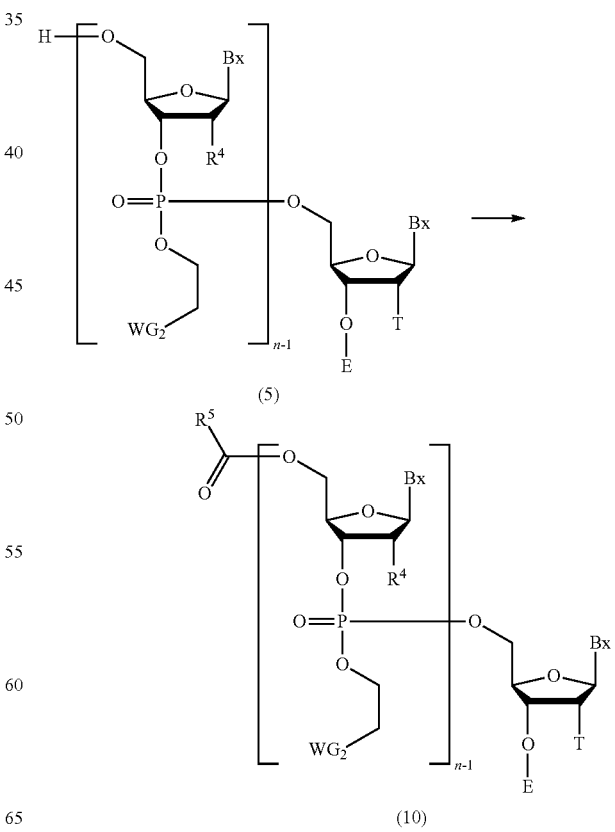

(5)

(10)

Wherein:

$B_x$, E, n, $R^4$, T and $WG^2$ are the same as defined above; and $R^5$ represents methyl or phenoxymethyl.

The step is a reaction for protecting the 5'-hydroxyl group unreacted in step (B), and can be performed by reacting a capping agent with a compound attached to the solid support. Examples of the "capping agent" may include acetic anhydride and phenoxyacetic anhydride. The capping agent to be used can be diluted in a suitable solvent so as to be of a concentration of 0.05 to 1 M. The solvent is not specifically limited unless it is involved in the reaction, and may include, for example, pyridine, dichloromethane, acetonitrile, tetrahydrofuran and mixtures thereof. In addition, for example, 4-dimethylaminopyridine, N-methylimidazole can be used as a reaction accelerator in the step, if necessary. The reaction temperature in the reaction is preferably in the range of 20° C. to 50° C. The reaction time varies depending on the kind of the capping agent and the reaction temperature, and is preferably between 1 and 30 minutes. The amount of the agent to be used is preferably in the range of 1 to 100 mol per mol of compound attached to the solid support, and more preferably 1 to 10 mol per mol of compound attached to the solid support.

(4) Step D:

Converting a phosphorous group into a phosphate group by reacting an oxidizing agent with compound (9) produced in step B.

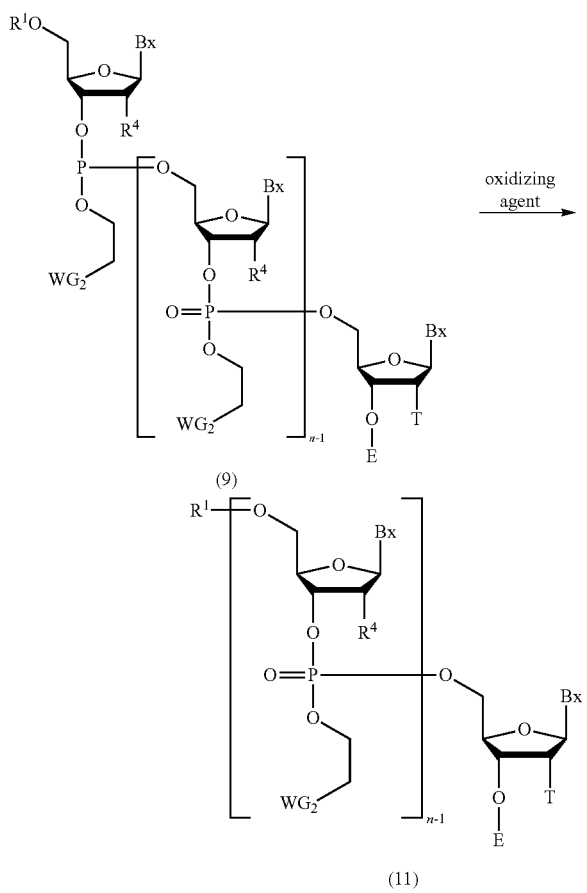

Wherein:

$B_x$, E, n, $R^1$, $R^4$, T and $WG^2$ are the same as defined above.

The step is a reaction for converting trivalent phosphorus to pentavalent phosphorus by using an oxidizing agent, and can be performed by reacting an oxidizing agent with a compound attached to the solid. Examples of the "oxidizing agent" may include iodine and tert-butyl hydroperoxide.

In addition, the oxidizing agent to be used can be diluted in a suitable solvent so as to be of a concentration of 0.05 to 1 M. The solvent is not specifically limited unless it is involved in the reaction, and may include, for example, pyridine, tetrahydrofuran, water and mixtures thereof. For example, iodine/water/pyridine-tetrahydrofuran, iodine/pyridine-acetic acid and a peroxidation agent (t-butylhydroperoxide/methylene chloride and the like) can be used. The reaction temperature is preferably in the range of 20° C. to 50° C. The reaction time varies depending on the kind of the oxidizing agent and the reaction temperature, and is preferably between 1 and 30 minutes. The amount of the agent to be used is preferably in the range of 1 to 100 mol per mol of compound attached to the solid support, and more preferably 1 to 50 mol per mol of compound.

(5) Step E:

Cleaving the compound (11) produced by step D from the solid support, and then removing the protecting groups of each nucleobase and each 2'-hydroxyl group.

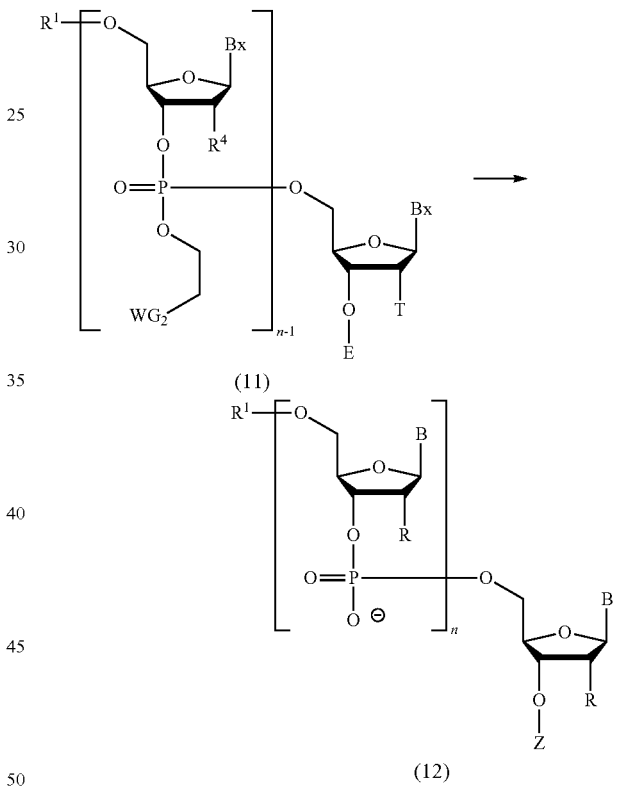

Wherein:

B, $B_x$, E, R, $R^1$, $R^4$, n, T, $WG^2$ and Z are the same as defined above.

The cleaving step is a reaction for cleaving an oligo-RNA having a desired chain length from the solid support and a linker with a cleaving agent, and is performed by adding a cleaving agent to the solid support which contains an oligo-RNA having a desired chain length.

In the step, the protecting group of a nucleobase can be removed. Examples of the "cleaving agent" may include concentrated aqueous ammonia and methylamine. The cleaving agent to be used in the step may be diluted by, for example, methanol, ethanol, isopropyl alcohol, acetonitrile, tetrahydrofuran and mixtures thereof. Among them, ethanol is preferable. The reaction temperature may be in the range of 15° C. to 75° C., preferably 15° C. to 30° C., and more preferably 18° C. to 25° C. The reaction time for deprotection may be in the range of 1 to 30 hours, preferably 1 to 24 hours, and more preferably 1 to 4 hours. The concentration of ammonium hydroxide in the solution to be used for deprotection may be 20 to 30% by weight, preferably 25 to 30% by weight, more preferably 28 to 30% by weight. The amount of the agent to be used may be in the range of 1 to 100 mol per mol of compound attached to the solid support, and preferably from 10- to 50-fold mol per mol of compound. The step for removing the protecting group of the 2'-hydroxyl group is performed by reacting the agent for removing the protecting group of the 2'-hydroxyl group such as tetrabutylammonium fluoride, trihydrogenfluoride/triethylamine salt. The solvent to be used is not specifically limited unless it is involved in the reaction, and may include, for example, tetrahydrofuran, N-methylpyrrolidone, pyridine, dimethylsulfoxide and mixtures thereof. If necessary, alkylamine, amidine, thiol, thiol derivatives or mixtures of these can be added as a compound scavenging the acrylonitrile which is a by-product in the step. Examples of the "alkylamine" may include a straight alkylamine having 1 to 6 carbon atoms. Specifically, the "alkylamine" may include, for example, methylamine, ethylamine, n-propylamine, n-butylamine, n-pentylamine and n-hexylamine. Examples of the "amidine" may include benzamidine and formamidine. Examples of the "thiol" may include a straight thiol having 1 to 6 carbon atoms. Specifically, the "thiol" may include, for example, methanethiol, ethanethiol, 1-propanethiol, 1-butanthiol, 1-pentanethiol and 1-hexanthiol. Examples of the "thiol derivative" may include the same or different alcohol and ether having a straight alkylthiol having 1 to 6 carbon atoms. Specifically, the thiol derivative may include, for example, 2-mercaptoethanol, 4-mercapto-1-butanol, 6-mercapto-1-hexanol, mercaptomethyl ether, 2-mercaptoethyl ether, 3-mercaptopropyl ether, 4-mercaptobutyl ether, 5-mercaptopentyl ether and 6-mercaptohexyl ether. The reaction temperature is preferably in the range of 20° C. to 80° C. The reaction time varies depending on the type of a deprotecting agent to be used and the reaction temperature, and is preferably in the range of 1 hour to 100 hours. The amount of the agent to be used is preferably in the range of 50 to 500 mol per mol of protecting group removed, and more preferably 50 to 100 mol per mol of protecting group removed. The oligo-RNA protected of the 5'-hydroxyl group can be isolated and purified from the above-mentioned reaction mixture by using a standard separation and purification technique such as extraction, concentration, neutralization, filtration, centrifugation, recrystallization, silica gel column chromatography, thin-layer chromatography, hydrophobic column chromatography, ion-exchange column chromatography, gel filtration column chromatography, dialysis, ultrafiltration and the like.

(6) Step F:

Removing the 5'-hydroxyl group of the compound (12) produced by step E.

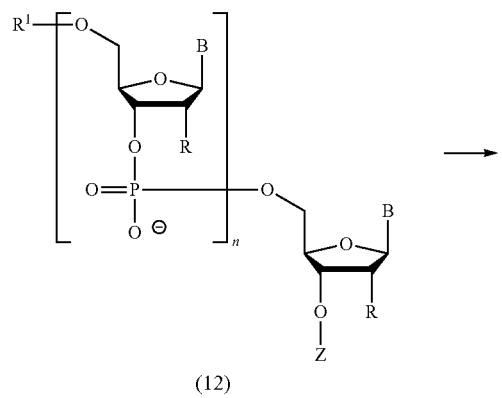

(12)

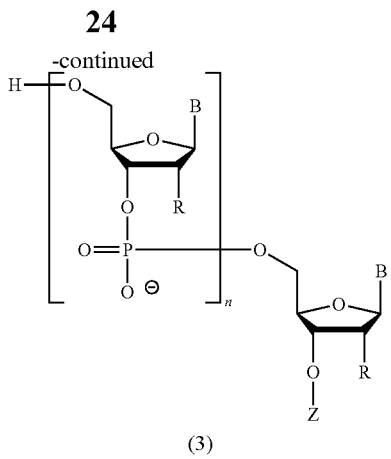

(3)

Wherein:

B, n, R, $R^1$ and Z are the same as defined above.

The step is a reaction for finally removing the protecting group of the 5'-hydroxyl group of the oligoribonucleotide, and can be performed by reacting an acid on the oligo-RNA cleaved from the solid support. Examples of the "acid" to be used in the step may include trichloroacetic acid, dichloroacetic acid and acetic acid. The acid diluted in a suitable solvent can be used in the step. The solvent is not specifically limited unless it is involved in the reaction, and may include, for example, dichloromethane, acetonitrile, water, a buffer wherein pH is in the range from 2 to 5 and mixtures thereof. Examples of the "buffer solution" may include an acetate buffer. The reaction temperature in the reaction is preferably in the range of 20° C. to 50° C. The reaction time varies depending on the kind of the acid and the reaction temperature, and is preferably between 1 minute and 1 hour.

The amount of the agent to be used is preferably in the range of 1 to 100 mol per mol of compound attached to the solid support, and more preferably 1 to 10 mol per mol of compound.

(7) Step G:

Isolating and purifying the compound (3) produced by step F.

The step of isolating and purifying is a step for isolating and purifying a desired oligo-RNA from the above reaction mixture with a known method for isolating and purifying which may include, for example, extraction, concentration, neutralization, filtration, centrifugal separation, recrystallization, reverse-phase column chromatography ($C_8$ to $C_{18}$), reverse phase cartridge column ($C_8$ to $C_{18}$), positive ion-exchange column chromatography, anion-exchange column chromatography, gel filtration column chromatography, high performance liquid chromatography, dialysis, ultrafiltration and combinations thereof. Examples of the "eluent" may include acetonitrile, methanol, ethanol, isopropyl alcohol, water and solvent mixed at an arbitrary ratio. In this case, for example, pH of the solution can be controlled to be in the range pH 1 to 9 by adding sodium phosphate, potassium phosphate, sodium chloride, potassium chloride, ammonium acetate, triethylammonium acetate, sodium acetate, potassium acetate, tris-hydrochloric acid or ethylenediaminetetraacetic acid as an additive in a concentration of 1 mM to 2 M. An oligo-RNA having a desired chain length can be produced by repeating steps A to D.

In addition, in the method, the compound (26a) wherein $R^4$ is the substituent (6), the compound (26a) wherein $R^4$ is H or acyloxy, or the compound (26b) wherein $R^2$ is alkyloxy etc. are used.

When using the compound (26a) wherein $R^4$ is H or acyloxy or the compound (26b) wherein $R^2$ is alkyloxy as a starting material, it is necessary to use one or more phosphoramidite compounds of the present invention as a nucleic acid monomer compound.

In addition, in the method, isolation and purification of an oligo-RNA is also performed by performing the operations of step F before performing the operations of step E, the operations of step E, and then the operations of step G.

EXAMPLES

The present invention will now be described in more detail with reference to Examples, to which, however, the present invention is not limited. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Chloromethyl 2-cyanoethylether

Step 1

Production of methylthiomethyl 2-cyanoethylether 3-hydroxypropionitrile (32 g, 450 mmol) was dissolved in 450 mL of dimethylsulfoxide, and 324 mL of acetic anhydride and 231 mL of acetic acid were added thereto, and the reaction solution was stirred at room temperature for 24 hours.

Sodium bicarbonate (990 g) was dissolved in 4.5 L of water, and the reaction solution was added to the aqueous sodium bicarbonate solution dropwise over 1 hour. The reaction solution was stirred for 1 hour, and was subjected to extraction with ethyl acetate, and the extract was dried over anhydrous magnesium sulfate, and the solvent was distilled off. The obtained oily product was purified by silica gel column chromatography to obtain 41 g of methylthiomethyl 2-cyanoethylether as a colorless oily product (yield 70%).

$^1$H-NMR (CDCl$_3$): 2.18 (s, 3H); 2.66 (t, 2H, J=6.3 Hz); 3.77 (t, 2H, J=6.3 Hz); 4.69 (s, 2H)

Step 2

Production of chloromethyl 2-cyanoethylether

Methylthiomethyl 2-cyanoethylether (3.3 g, 25 mmol) was dissolved in 70 mL of methylene chloride, and 2 mL of sulfuryl chloride (25 mmol) was added dropwise, and the reaction was further performed at room temperature for 1 hour.

After the reaction completed, the solvent was distilled off under reduced pressure to obtain 2.5 g of the objective compound as a colorless oily product (yield 85%).

Boiling point: 84-85° C. (0.3 Torr)

$^1$H-NMR (CDCl$_3$): 2.72 (t, 2H, J=6.3 Hz); 3.92 (t, 2H, J=6.3 Hz); 5.52 (s, 2H)

Example 2

5'-O-(4,4'-Dimethoxytrityl)-2'-O-(2-cyanoethoxymethyl)uridine 3'-O-(2-cyanoethyl N,N-diisopropylphosphoramidite)

Step 1

Production of 5'-O-(4,4'-dimethoxytrityl)-2'-O-(2-cyanoethoxymethyl)uridine

5'-O-(4,4'-Dimethoxytrityl)uridine (546 mg, 1 mmol) was dissolved in 4 mL of 1,2-dichloroethane, and 452 mg of diisopropylethylamine (3.5 mmol) was added thereto, and 365 mg of dibutylstannyl dichloride (1.2 mmol) was further added thereto. The reaction was performed at room temperature for 1 hour.

Subsequently, the reaction was performed at 80° C., and 155.4 mg of chloromethyl 2-cyanoethylether (1.3 mmol) was added dropwise, and the reaction solution was stirred for 30 minutes.

After the reaction completed, the reaction solution was added into an aqueous saturated sodium bicarbonate solution, and was subjected to extraction with methylene chloride, and the extract was dried over anhydrous magnesium sulfate, and the solvent was distilled off.

The obtained mixture was purified by 30 g of silica gel column chromatography to obtain 5'-O-(4,4'-dimethoxytrityl)-2'-O-(2-cyanoethoxymethyl)uridine (197 mg; yield 34%).

$^1$H-NMR (CDCl$_3$): 2.47 (d, 1H, J=7.8 Hz); 2.69 (t, 2H, J=6.3 Hz); 3.55 (dd, 1H, J=11.3, 2.2 Hz); 3.62 (dd, 1H, J=11.3, 2.2 Hz); 3.83 (s, 6H); 3.87 (t, 2H, J=6.3 Hz); 4.07-4.08 (m, 1H); 4.32 (dd, 1H, J=5.3, 1.9 Hz); 4.54 (q, 1H, J=5.3 Hz); 4.94, 5.11 (2d, 2H, J=6.9 Hz); 5.32 (d, 1H, J=8.2 Hz); 6.00 (d, 1H, J=1.9 Hz); 6.85-6.88 (m, 4H); 7.29-7.41 (m, 9H); 8.02 (d, 1H, J=8.2 Hz); 8.53 (br.s, 1H)

ESI-Mass: 652 [M+Na]$^+$

Step 2

Production of 5'-O-(4,4'-dimethoxytrityl)-2'-O-(2-cyanoethoxymethyl)uridine 3'-O-(2-cyanoethyl N,N-diisopropyl phosphoramidite)

5'-O-(4,4'-Dimethoxytrityl)-2'-O-(2-cyanoethoxymethyl) uridine (209 g, 0.332 mmol) was dissolved in 2 mL of acetonitrile obtained in Step 1 and 23 mg of tetrazole (0.332 mmol), and 150 mg of 2-cyanoethyl N,N,N',N'-tetraisopropyl phosphorodiamidite (0.498 mmol) were added dropwise, and the reaction was performed at 45° C. for 1.5 hours.

After the reaction completed, the reaction solution was mixed with an aqueous saturated sodium bicarbonate solution, and was subjected to extraction with ethyl acetate, and the extract was dried over anhydrous magnesium sulfate, and the solvent was distilled off. The obtained mixture was purified by 20 g of silica gel column chromatography to obtain the objective compound (200 mg; yield 73%).

ESI-Mass: 852 [M+Na]$^+$

Example 3

2'-O-(2-Cyanoethoxymethyl)uridine

Step 1

Production of 3',5'-O-(tetraisopropyldisiloxan-1,3-diyl)-2'-O-(2-cyanoethoxymethyl)uridine 3',5'-O-(Tetraisopropyldisiloxan-1,3-diyl)uridine (150 mg, 0.3 mmol) was dissolved in 7 mL of tetrahydrofuran under an argon atmosphere, and 54 mg of methylthiomethyl 2-cyanoethylether (0.4 mmol) and 100 mg of molecular sieves 4A were added, and the reaction solution was stirred for 10 minutes.

The reaction was performed at 0° C., and 2 mL of a solution of trifluoromethanesulfonic acid (10 mg, 0.06 mmol) in tetrahydrofuran was added. Then, 92 mg of N-iodosuccinimide (0.4 mmol) was added, and the reaction solution was stirred for 1 hour.

After the reaction completed, the reaction solution was filtrated with a celite and washed with methylene chloride, and the obtained organic layer was washed with 1 M aqueous sodium hydrogen thiosulfate solution. The organic layer was washed with aqueous saturated sodium bicarbonate solution, and dried over anhydrous magnesium sulfate, and the solvent was distilled off.

The obtained residue was purified by thin-layer chromatography to obtain 3',5'-O-(tetraisopropyldisiloxan-1,3-diyl)-2'-O-(2-cyanoethoxymethyl)uridine (150 mg; yield 85%).

$^1$H-NMR (CDCl$_3$): 0.97-1.12 (m, 28H); 2.68-2.73 (m, 2H) 3.78-3.86 (m, 1H); 3.96-4.05 (m, 2H); 4.12-4.30 (m, 4H); 5.0-5.04 (m, 2H); 5.70 (d, 1H, J=8.2 Hz); 5.75 (s, 1H); 7.90 (d, 1H, J=8.2 Hz); 9.62 (br.s, 1H)

ESI-Mass: 570 [M+H]$^+$

Step 2

Production of 2'-O-(2-cyanoethoxymethyl)uridine

3',5'-O-(Tetraisopropyldisiloxan-1,3-diyl)-2'-O-(2-cyanoethoxymethyl)uridine (200 mg, 0.35 mmol) obtained in step 1 was dissolved in 2 mL of methanol, and 65 mg of ammonium fluoride (1.76 mmol) was added thereto, and the reaction solution was stirred with heating at 50° C. for 5 hours.

After air-cooling, acetonitrile is added to the reaction solution. The solution was stirred, and was filtrated and concentrated.

The obtained residue was purified by silica gel column chromatography to obtain the objective compound (108 mg; yield 94%).

$^1$H-NMR (CD$_3$OD): 2.72-2.76 (t, 2H, J=6.2 Hz); 3.68-3.92 (m, 4H); 4.00-4.03 (m, 1H); 4.26-4.32 (m, 2H); 4.81-4.95 (m, 2H); 5.71 (d, 1H, J=8.1 Hz); 6.00 (d, 1H, J=3.3 Hz); 8.10 (d, 1H, J=8.1 Hz)

ESI-Mass: 350 [M+Na]$^+$

Example 4

Production of 5'-O-(4,4'-dimethoxytrityl)-2'-O-(2-cyanoethoxymethyl)uridine

2'-O-(2-Cyanoethoxymethyl)uridine (14 g, 43 mmol) was subjected to azeotropic distillation with pyridine, and then was dried with a vacuum pump for 30 minutes.

The residue was dissolved in 300 mL of tetrahydrofuran, and 68 g of pyridine (856 mmol) and 20 g of molecular sieves 4A were added under an argon atmosphere, and the mixture was stirred for 10 minutes.

To the reaction solution was added 19.6 g of 4,4'-dimethoxytritylchloride (57.8 mmol) by 3 portions every 1 hour, and the mixture was further stirred for 1 hour.

After 10 mL of methanol was added and the reaction solution was stirred for 2 minutes, the reaction solution was filtrated with a celite, and was washed with ethyl acetate.

After concentrating the filtrate, the residue was dissolved in ethyl acetate, and was washed with a saturated aqueous sodium bicarbonate solution.

After the organic layer was washed with a saturated brine and dried over anhydrous magnesium sulfate, the solvent was distilled off.

The obtained residue was purified by silica gel chromatography to obtain the objective compound (26.5 g, yield 98%).

Example 5

N$^4$-Acetyl-5'-O-(4,4'-dimethoxytrityl)-2'-O-(2-cyanoethoxymethyl)cytidine 3'-O-(2-cyanoethyl N,N-diisopropyl phosphoramidite)

Step 1

Production of N$^4$-acetyl-5'-O-(4,4-dimethoxytrityl)-2'-O-(2-cyanoethoxymethyl)cytidine N$^4$-Acetyl-5'-O-(4,4'-dimethoxytrityl)cytidine (588 mg, 1 mmol) was dissolved in 4 mL of 1,2-dichloroethane, and 452 mg of diisopropylethylamine (3.5 mmol) was added thereto, and then 365 mg of dibutylstannyl dichloride (1.2 mmol) was further added. The reaction was performed at room temperature for 1 hour.

Then, the reaction was performed at 80° C., and 155.4 mg of chloromethyl 2-cyanoethylether (1.3 mmol) was added dropwise, and the reaction solution was stirred for 60 minutes.

After the reaction completed, the reaction solution was added into an aqueous saturated sodium bicarbonate solution, and was extracted with methylene chloride. The extract was dried over anhydrous magnesium sulfate, and the solvent was distilled off. The obtained mixture was purified by 30 g of silica gel column chromatography to obtain N$^4$-acetyl-5'-O-(4,4'-dimethoxytrityl)-2'-O-(2-cyanoethoxymethyl)cytidine (219 mg; yield 35%).

$^1$H-NMR (CDCl$_3$): 2.19 (s, 3H); 2.56 (d, 1H, J=8.8 Hz); 2.65 (t, 2H, J=6.2 Hz); 3.55 (dd, 1H, J=10.5, 2.5 Hz); 3.63 (dd, 1H, J=10.5, 2.5 Hz); 3.82 (s, 6H); 3.86 (t, 2H, J=6.2 Hz); 4.09-4.14 (m, 1H); 4.28 (d, 1H, J=5.1 Hz); 4.44-4.49 (m, 1H); 4.97, 5.24 (2d, 2H, J=6.9 Hz); 5.96 (s, 1H); 6.86-6.88 (m, 4H); 7.09 (d, 1H, J=6.9 Hz); 7.26-7.42 (m, 9H); 8.48 (d, 1H, J=6.9 Hz); 8.59 (br.s, 1H)

ESI-Mass: 693 [M+Na]$^+$

Step 2

Production of N$^4$-acetyl-5'-O-(4,4'-dimethoxytrityl)-2'-O-(2-cyanoethoxymethyl)cytidine 3'-O-(2-cyanoethyl N,N-diisopropylphosphoramidite)

N$^4$-Acetyl-5'-O-(4,4'-dimethoxytrityl)-2'-O-(2-cyanoethoxymethyl)cytidine (205 mg, 0.306 mmol) obtained in Step 1 was dissolved in 2 mL of methylene chloride, and 105 mg of diisopropylethylamine (0.812 mmol) was added, and 116 mg of 2-cyanoethyl N,N-diisopropyl chlorophosphoramidite (0.49 mmol) was added dropwise. The reaction solution was reacted at room temperature for 1 hour.

After the reaction completed, the solvent was distilled off, and the obtained mixture was purified by 20 g of silica gel column chromatography to obtain the objective compound (242 mg; yield 91%).

ESI-Mass: 871 [M+H]$^+$

Example 6

N⁴-Acetyl-2'-O-(2-cyanoethoxymethyl)cytidine

Step 1

Production of N⁴-acetyl-3',5'-O-(tetraisopropyldisiloxan-1,3-diyl)-2'-O—(2-cyanoethoxymethyl)cytidine N⁴-Acetyl-3',5'-O-(tetraisopropyldisiloxan-1,3-diyl)cytidine (1.00 g, 1.89 mmol) and methylthiomethyl 2-cyanoethylether (500 mg, 3.79 mmol) were mixed, and the mixture was dissolved in a mixed solvent of 10 mL of toluene and 10 mL of tetrahydrofuran.

Subsequently, 975 mg of silver trifluoromethanesulfonate was added and was dried by adding molecular sieves 4A.

Under ice cooling, 370 mg of N-bromosuccinimide (2.08 mmol) was added, and the solution was stirred for 10 minutes in the reaction vessel shielded from light. Furthermore, 70 mg of N-bromosuccinimide (0.39 mmol) was added and stirred for 25 minutes.

After the reaction completed, the reaction solution was diluted with methylene chloride, and was washed with an aqueous saturated sodium bicarbonate solution. The extract was dried over anhydrous sodium sulfate, and the solvent was distilled off. The obtained mixture was purified by silica gel column chromatography to obtain N⁴-acetyl-3',5'-O-(tetraisopropyldisiloxan-1,3-diyl)-2'-O-(2-cyanoethoxymethyl)cytidine (936 mg; yield 81%).

$^1$H-NMR (CDCl$_3$): 0.90-1.11 (m, 28H); 2.28 (s, 3H); 2.62-2.79 (m, 2H); 3.78-3.89 (m, 1H); 3.96-4.04 (m, 2H); 4.19-4.23 (m, 3H); 4.30 (d, 1H, J=13.6 Hz); 5.00 (d, 1H, J=6.8 Hz); 5.09 (d, 1H, J=6.8 Hz); 5.77 (s, 1H); 7.44 (d, 1H, J=7.5 Hz); 8.30 (d, 1H, J=7.5 Hz); 10.13 (s, 1H)

ESI-Mass: 611 [M+H]$^+$

Step 2

Production of N⁴-acetyl-2'-O-(2-cyanoethoxymethyl)cytidine

N⁴-Acetyl-3',5'-O-(tetraisopropyldisiloxan-1,3-diyl)-2'-O-(2-cyanoethoxymethyl)cytidine (500 mg, 0.819 mmol) obtained in step 1 was dissolved in a mixed solvent of 2.5 mL of tetrahydrofuran and 2.5 mL of methanol, and 150 mg of ammonium fluoride (4.10 mmol) was added, and then the reaction solution was reacted at 50° C. for 4 hours.

After the reaction completed, the reaction solution was diluted with acetonitrile and filtrated, and the solvent was distilled off. The obtained mixture was purified by silica gel column chromatography to obtain the objective compound (210 mg; yield 70%).

$^1$H-NMR (D$_2$O): 2.13 (s, 3H); 2.66-2.71 (m, 2H); 3.72-3.78 (m, 3H); 3.90 (dd, 1H, J=13.0, 2.6 Hz); 4.06-4.11 (m, 1H); 4.20 (dd, 1H, J=7.1, 5.2 Hz); 4.29 (dd, 1H, J=5.1, 2.9 Hz); 4.83 (d, 1H, J=7.2 Hz); 4.94 (d, 1H, J=7.2 Hz); 5.95 (d, 1H, J=2.9 Hz); 7.25 (d, 1H, J=7.6 Hz); 8.25 (d, 1H, J=7.6 Hz)

ESI-Mass: 391 [M+Na]$^+$

Example 7

Production of N⁴-acetyl-5'-O-(4,4'-dimethoxytrityl)-2'-O-(2-cyanoethoxymethyl)cytidine 2'-O-(2-Cyanoethoxymethyl)cytidine (9.9 g, 26.8 mmol) was subjected to azeotropic distillation with pyridine, and then was dried with a vacuum pump for 30 minutes. The residue was dissolved in 190 mL of tetrahydrofuran, and 43 g of pyridine (538 mmol) and 20 g of molecular sieves 4A were added under an argon atmosphere, and the mixture was stirred for 10 minutes.

To the reaction solution was added 11.8 g of 4,4'-dimethoxytritylchloride (34.9 mmol) by 3 portions every 1 hour, and the mixture was further stirred for 1 hour.

After 2 mL of methanol was added and the reaction solution was stirred for 2 minutes, the reaction solution was filtrated with a celite, and was washed with ethyl acetate.

After concentrating the filtrate with evaporation, the residue was dissolved in ethyl acetate, and was washed with a saturated aqueous sodium bicarbonate solution. After the organic layer was washed with a saturated brine and dried over anhydrous magnesium sulfate, and the solvent was distilled off.

The obtained residue was purified by silica gel chromatography to obtain the objective compound (15 g; yield 83%).

Example 8

N²-Acetyl-5'-O-(4,4'-dimethoxytrityl)-2'-O-(2-cyanoethoxymethyl)guanosine 3'-O-(2-cyanoethyl N,N-diisopropylphosphoramidite)

Step 1

Production of N²-acetyl-5'-O-(4,4'-dimethoxytrityl)-2'-O-(2-cyanoethoxymethyl)guanosine N²-Acetyl-5'-O-(4,4'-dimethoxytrityl)guanosine (627 mg, 1 mmol) was dissolved in 4 mL of 1,2-dichloroethane, and 452 mg of diisopropylethylamine (3.5 mmol) was added, and then 365 mg of dibutylstannyl dichloride (1.2 mmol) was added. And then, the reaction solution was reacted at room temperature for 1 hour.

Then, the reaction solution was heated up to 80° C., and 155.4 mg of chloromethyl 2-cyanoethylether (1.3 mmol) was added dropwise, and the solution was stirred for 60 minutes.

After the reaction completed, the reaction solution was mixed with an aqueous saturated sodium bicarbonate solution, and was subjected to extraction with methylene chloride. The extract was dried over anhydrous magnesium sulfate, and the solvent was distilled off. The obtained mixture was purified by 30 g of silica gel column chromatography to obtain N²-acetyl-5'-O-(4,4'-dimethoxytrityl)-2'-O-(2-cyanoethoxymethyl)guanosine (450 mg; yield 63%).

$^1$H-NMR (CDCl$_3$): 1.92 (s, 3H); 2.47-2.51 (m, 2H); 2.68 (br.s, 1H); 3.30 (dd, 1H, J=10.7, 3.8 Hz); 3.47 (dd, 1H, J=10.7, 3.8 Hz); 3.55-3.60 (m, 1H); 3.65-3.70 (m, 1H); 3.74, 3.75 (2 s, 6H); 4.22-4.23 (m, 1H); 4.55-4.58 (m, 1H); 4.78, 4.83 (2d, 2H, J=7.0 Hz); 5.01 (t, 1H, J=5.1 Hz); 5.99 (d, 1H, J=5.1 Hz); 6.76-6.79 (m, 4H); 7.17-7.44 (m, 9H); 7.88 (s, 1H); 8.36 (br.s, 1H) 12.06 (br.s, 1H)

Step 2

Production of N²-acetyl-5'-O-(4,4'-dimethoxytrityl)-2'-O-(2-cyanoethoxymethyl)guanosine 3'-O-(2-cyanoethyl N,N-diisopropylphosphoramidite)

N²-Acetyl-5'-O-(4,4'-dimethoxytrityl)-2'-O-(2-cyanoethoxymethyl)guanosine (400 mg, 0.563 mmol) obtained in step 1 was dissolved in 2 mL of methylene chloride, and 181 mg of diisopropylethylamine (1.4 mmol) was added, and 161 mg of 2-cyanoethyl N,N-diisopropylchloro phosphoramidite (0.68 mmol) was added dropwise. Then, the reaction was performed at room temperature for 1 hour. After the reaction completed, the solvent was distilled off and the obtained mixture was purified by 20 g of silica gel column chromatography to obtain the objective compound (471 mg; yield 92%).

Example 9

N[6]-Acetyl-5'-O-(4,4'-dimethoxytrityl)-2'-O-(2-cyanoethoxymethyl)adenosine 3'-O-(2-cyanoethyl N,N-diisopropylphosphoramidite)

Step 1

Production of N[6]-acetyl-5'-O-(4,4'-dimethoxytrityl)-2'-O-(2-cyanoethoxymethyl)adenosine N[6]-Acetyl-5'-O-(4,4'-dimethoxytrityl)adenosine (22.0 g, 36.0 mmol) was dissolved in 170 mL of 1,2-dichloroethane, and 16.3 g of diisopropylethylamine (126 mmol) was added, and 12.1 g of dibutylstannyl dichloride (39.7 mmol) was added subsequently. Then, the reaction was performed at room temperature for 1 hour.

Then, the reaction solution was heated up to 80° C., and 4.30 g of chloromethyl 2-cyanoethylether (36.0 mmol) was added dropwise, and the solution was stirred for 30 minutes.

After the reaction completed, the reaction solution was added to an aqueous saturated sodium bicarbonate solution, and was subjected to extraction with methylene chloride. The extract was dried over anhydrous magnesium sulfate, and the solvent was distilled off. The obtained mixture was purified by silica gel column chromatography to obtain N[6]-acetyl-5'-O-(4,4'-dimethoxytrityl)-2'-O-(2-cyanoethoxymethyl)adenosine (7.47 g; yield 33%).

$^1$H-NMR (CDCl$_3$): 2.51 (t, 2H, J=6.2 Hz); 2.58 (d, 1H, J=5.5 Hz); 2.61 (s, 3H); 3.45 (dd, 1H, J=10.7, 4.0 Hz); 3.54 (dd, 1H, J=10.7, 3.2 Hz); 3.62-3.79 (m, 2H); 3.79 (s, 6H); 4.25 (br.q, 1H, J=4.6 Hz); 4.59 (q, 1H, J=5.2 Hz); 4.87-4.94 (m, 3H); 6.23 (d, 1H, J=4.4 Hz); 6.80-6.83 (m, 4H); 7.22-7.32 (m, 7H); 7.40-7.43 (m, 2H); 8.20 (s, 1H); 8.61 (br.s, 1H); 8.62 (s, 1H)

ESI-Mass: 695 [M+H]$^+$

Step 2

Production of N[6]-acetyl-5'-O-(4,4'-dimethoxytrityl)-2'-O-(2-cyanoethoxymethyl)adenosine 3'-O-(2-cyanoethyl N,N-diisopropylphosphoramidite)

N[6]-Acetyl-5'-O-(4,4'-dimethoxytrityl)-2'-O-(2-cyanoethoxymethyl)adenosine (10.0 g, 14.4 mmol) obtained in step 1 was dissolved in 75 mL of methylene chloride, and 4.7 g of diisopropylethylamine (36 mmol) was added, and 4.82 g of 2-cyanoethyl N,N-diisopropylchloro phosphoramidite (20.3 mmol) was added dropwise. Then, the reaction was performed at room temperature for 1 hour.

After the reaction completed, the solvent was distilled off and the obtained mixture, in which about 30 mL of the solvent remained, was purified by silica gel column chromatography to obtain the objective compound (12.0 g; yield 93%).

ESI-Mass: 895 [M+H]$^+$

Example 10

N[6]-Acetyl-2'-O-(2-cyanoethoxymethyl)adenosine

Step 1

Production of N[6]-acetyl-3',5'-O-(tetraisopropyldisiloxan-1,3-diyl)-2'-O-(2-cyanoethoxymethyl)adenosine To 8 mL of methylene chloride was suspended 245 mg of N-iodosuccinimide (1.09 mmol) and 280 mg of silver trifluoromethanesulfonate (1.09 mmol), and the solution was dried by adding molecular sieves 4A.

To the reaction solution was added a solution of N[6]-acetyl-3',5'-O-(tetraisopropyldisiloxan-1,3-diyl) adenosine (400 mg, 0.73 mmol) and 145 mg of methylthiomethyl 2-cyanoethylether (1.11 mmol) in 4 mL of methylene chloride under ice cooling, and the reaction mixture was stirred for 3 hours.

After the reaction completed, the reaction mixture was diluted with methylene chloride, and was washed with aqueous sodium thiosulfate solution and aqueous saturated sodium bicarbonate solution. The extract was dried over anhydrous magnesium sulfate, and the solvent was distilled off. The obtained mixture was purified by silica gel column chromatography to obtain N[6]-acetyl-3',5'-O-(tetraisopropyldisiloxan-1,3-diyl)-2'-O-(2-cyanoethoxymethyl)adenosine (201 mg; yield 45%).

$^1$H-NMR (CDCl$_3$): 0.98-1.11 (m, 28H); 2.62 (s, 3H); 2.69 (td, 2H, 6.5, J=1.5 Hz); 3.81-3.89 (m, 1H); 4.02-4.09 (m, 2H); 4.17 (d, 1H, J=9.4 Hz); 4.28 (d, 1H, J=13.4 Hz); 4.50 (d, 1H, J=4.5 Hz); 4.67 (dd, 1H, J=8.8, 4.5 Hz); 5.02 (d, 1H, J=7.0 Hz); 5.08 (d, 1H, J=7.0 Hz); 6.10 (s, 1H); 8.34 (s, 1H); 8.66 (s, 1H); 8.67 (s, 1H)

ESI-Mass: 636 [M+H]$^+$

Step 2

Production of N[6]-acetyl-2'-O-(2-cyanoethoxymethyl)adenosine

N[6]-Acetyl-3',5'-O-(tetraisopropyldisiloxan-1,3-diyl)-2'-O-(2-cyanoethoxymethyl)adenosine (300 mg, 0.47 mmol) obtained in step 1 was dissolved in a mixed solvent of 0.1 mL of acetic acid and 2 mL of 0.5 M tetrabutylammonium fluoride solution, and the reaction solution was stirred at room temperature for 2 hours.

After the reaction completed, the obtained reaction mixture was purified by silica gel column chromatography to obtain the objective compound (160 mg; yield 86%).

$^1$H-NMR (DMSO-d): 2.25 (s, 3H); 2.53-2.68 (m, 2H); 3.41-3.46 (m, 1H); 3.56-3.64 (m, 2H); 3.69-3.73 (m, 1H); 4.00-4.01 (m, 1H); 4.36-4.37 (m, 1H); 4.72-4.78 (m, 3H); 5.20 (bt, 2H); 5.41 (d, 1H, J=5.2 Hz); 6.17 (d, 1H, J=5.7 Hz); 8.66 (s, 1H); 8.72 (s, 1H); 10.72 (s, 1H)

ESI-Mass: 415 [M+Na]$^+$

Example 11

Production of N[6]-acetyl-5'-O-(4,4'-dimethoxytrityl)-2'-O-(2-cyanoethoxymethyl)adenosine N[6]-Acetyl-2'-O-(2-cyanoethoxymethyl)adenosine (9.50 g, 24.2 mmol) was dissolved in 100 mL of dehydrated pyridine, and then was dried by concentration. Then, the residue was dissolved in 100 mL of dehydrated pyridine under an argon atmosphere.

Under ice cooling, 10.7 g of 4,4'-dimethoxytrityl chloride (31.2 mmol) was added, and the reaction was performed at room temperature for 1 hour and 20 minutes. After the reaction completed, the reaction solution was diluted with methylene chloride, and was washed with water. The extract was dried over anhydrous sodium sulfate, and the solvent was distilled off. The obtained mixture was purified by silica gel column chromatography to obtain the objective compound (13.8 g; yield 82%).

Example 12

$N^2$-Phenoxyacetyl-5'-O-(4,4'-dimethoxytrityl)-2'-O-(2-cyanoethoxymethyl)guanosine 3'-O-(2-cyanoethyl N,N-diisopropylphosphoramidite)

Step 1

Production of $N^2$-phenoxyacetyl-5'-O-(4,4'-dimethoxytrityl)-2'-O-(2-cyanoethoxymethyl)guanosine $N^2$-Phenoxyacetyl-5'-O-(4,4'-dimethoxytrityl)guanosine (720 mg, 1 mmol) was dissolved in 4 mL of 1,2-dichloroethane, and 452 mg of diisopropylethylamine (3.5 mmol) was added, and 365 mg of dibutylstannyl dichloride (1.2 mmol) was added subsequently. Then, the reaction was performed at room temperature for 1 hour. Then, the reaction was performed at 80° C., and 155.4 mg of chloromethyl 2-cyanoethylether (1.3 mmol) was added dropwise, and the solution was stirred for 60 minutes. After the reaction completed, the reaction solution was mixed with an aqueous saturated sodium bicarbonate solution, and was subjected to extraction with methylene chloride. The extract was dried over anhydrous magnesium sulfate, and the solvent was distilled off. The obtained mixture was purified by 30 g of silica gel column chromatography to obtain $N^2$-phenoxyacetyl-5'-O-(4,4'-dimethoxytrityl)-2'-O-(2-cyanoethoxymethyl)guanosine (384 mg; yield 48%).

$^1$H-NMR (CDCl$_3$): 2.47-2.51 (m, 2H); 2.58 (br.s, 1H); 3.42 (dd, 1H, J=10.1, 3.8 Hz); 3.46 (dd, 1H, J=10.1, 3.8 Hz); 3.53-3.57 (m, 1H); 3.69-3.73 (m, 1H); 3.77 (s, 6H); 4.24-4.26 (m, 1H); 4.48-4.50 (m, 1H); 4.61-4.65 (m, 2H); 4.83, 4.87 (2d, 2H, J=7.0 Hz); 4.88 (t, 1H, J=5.7 Hz); 6.05 (d, 1H, J=5.7 Hz); 6.80-6.82 (m, 4H); 6.92-6.96 (m, 3H); 7.07-7.11 (m, 2H); 7.20-7.42 (m, 9H); 7.84 (s, 1H); 8.99 (s, 1H); 11.81 (br.s, 1H)

ESI-Mass: 825 [M+Na]$^+$

Step 2

Production of $N^2$-phenoxyacetyl-5'-O-(4,4'-dimethoxytrityl)-2'-O-(2-cyanoethoxymethyl)guanosine 3'-O-(2-cyanoethyl N,N-diisopropylphosphoramidite)

$N^2$-Phenoxyacetyl-5'-O-(4,4'-dimethoxytrityl)-2'-O-(2-cyanoethoxymethyl)guanosine (320 mg, 0.399 mmol) obtained in step 1 was dissolved in 4 mL of methylene chloride, and 128.8 mg of diisopropylethylamine (0.996 mmol) was added, and 141.5 mg of 2-cyanoethyl N,N-diisopropylchlorophosphoramidite (0.598 mmol) was added dropwise. Then, the reaction was performed at room temperature for 1 hour.

After the reaction completed, the solvent was distilled off and the obtained mixture was purified by 30 g of silica gel column chromatography to obtain the objective compound (316 mg; yield 79%).

ESI-Mass: 1003 [M+H]$^+$

Example 13

$N^2$-Phenoxyacetyl-2'-O-(2-cyanoethoxymethyl)guanosine

Step 1

Production of $N^2$-phenoxyacetyl-3',5'-O-(tetraisopropyl disiloxan-1,3-diyl)-2'-O-(2-cyanoethoxymethyl) guanosine $N^2$-Phenoxyacetyl-3',5'-O-(tetraisopropyldisiloxan-1,3-diyl)guanosine (2.0 g, 3.0 mmol) was dissolved in 16 mL of tetrahydrofuran, and 0.99 g of methylthiomethyl 2-cyanoethylether (7.6 mmol) and 1.0 g of molecular sieves 4A were added, and the reaction solution was stirred at −45° C. for 10 minutes under an argon atmosphere.

After a solution of 0.68 g of trifluoromethanesulfonic acid (4.5 mmol) in 5 mL of tetrahydrofuran was added and the reaction solution was stirred, 1.02 g of N-iodosuccinimide (4.5 mmol) was added, and the reaction solution was stirred for 15 minutes.

After saturated aqueous sodium bicarbonate solution was added to the reaction solution and then the reaction solution was filtrated, the organic layer was washed with 1 M aqueous sodium hydrogen thiosulfate solution. Further, the reaction solution was washed with water and saturated brine sequentially, and the extract was dried over anhydrous magnesium sulfate, and the solvent was distilled off.

The obtained residue was purified by silica gel chromatography to obtain $N^2$-phenoxyacetyl-3',5'-O-(tetraisopropyldisiloxan-1,3-diyl)-2'-O-(2-cyanoethoxymethyl)guanosine (2.0 g; yield 89%).

$^1$H-NMR (CDCl$_3$): 0.99-1.11 (m, 28H); 2.59-2.77 (m, 2H) 3.82-4.05 (m, 3H); 4.15 (d, 1H, J=9.3 Hz); 4.25-4.35 (m, 2H); 4.52-4.56 (dd, 1H, J=9.3, 4.3 Hz); 5.00-5.07 (2d, 2H, J=7.2 Hz); 5.95 (s, 1H), 6.99-7.12 (m, 3H); 7.35-7.40 (m, 2H); 8.09 (s, 1H); 9.38 (br.s, 1H) 11.85 (br.s, 1H)

ESI-Mass: 766 [M+Na]$^+$

Step 2

Production of $N^2$-phenoxyacetyl-2'-O-(2-cyanoethoxymethyl) guanosine

A solution consisting of 0.14 mL of acetic acid (0.14 mmol) and 2.83 mL of 1 M tetrabutylammonium fluoride in tetrahydrofuran (2.83 mmol) was prepared. $N^2$-Phenoxyacetyl-3',5'-O-(tetraisopropyldisiloxan-1,3-diyl)-2'-O-(2-cyanoethoxymethyl)guanosine (1.0 g, 1.35 mmol) obtained in step 1 was dissolved in 2.83 mL of tetrahydrofuran, and the solution prepared above was added, and the reaction was performed at room temperature for 1 hour under an argon atmosphere.

The reaction solution was concentrated under reduced pressure, and the residue was dissolved in methylene chloride, and was purified by silica gel column chromatography to obtain the objective compound (0.67 g; yield 99%).

$^1$H-NMR (DMSO-d$^6$): 2.59-2.66 (m, 2H); 3.41-3.63 (m, 4H); 3.98 (m, 1H); 4.32 (m, 1H); 4.58-4.62 (t, 1H, J=5.3 Hz); 4.71-4.78 (dd, 2H, J=13.1, 6.8 Hz); 4.87 (s, 2H); 5.12 (s, 1H) 5.37 (s, 1H); 5.97 (d, 1H, J=6.1 Hz) 6.96-6.99 (m, 3H); 7.28-7.34 (m, 2H); 8.30 (s, 1H); 11.78 (br.s, 2H)

ESI-Mass: 500 [M−H]$^+$

Example 14

N²-Phenoxyacetyl-5'-O-(4,4'-dimethoxytrityl)-2'-O-(2-cyanoethoxymethyl)guanosine N²-Phenoxyacetyl-2'-O-(2-cyanoethoxymethyl)guanosine (660 mg, 1.32 mmol) was subjected to azeotropic distillation with pyridine, and then was dried with a vacuum pump for 30 minutes.

The residue was dissolved in 9 mL of tetrahydrofuran, and 2.1 g of pyridine (26.4 mmol) and 600 mg of molecular sieves 4A were added under an argon atmosphere, and the reaction solution was stirred for 10 minutes.

To the reaction solution was added 540 mg of 4,4'-dimethoxytritylchloride (1.58 mmol) by 3 portions every 1 hour, and the reaction solution was further stirred for 1 hour.

After 2 mL of methanol was added and the reaction solution was stirred for 2 minutes, the reaction solution was filtrated with a celite, and was washed with ethyl acetate.

After concentrating the filtrate with evaporation, the residue was dissolved in ethyl acetate, and was separated with a saturated aqueous sodium bicarbonate solution. After the organic layer was washed with a saturated brine and dried over anhydrous magnesium sulfate, the solvent was distilled off.

The obtained residue was purified by silica gel chromatography to obtain the objective compound (800 mg; yield 75%).

Example 15

N⁶-Acetyl-3',5'-O-(tetraisopropyldisiloxan-1,3-diyl)-2'-O-(2-cyanoethoxymethyl)adenosine Step 1

Production of N⁶-acetyl-3',5'-O-(tetraisopropyldisiloxan-1,3-diyl)-2'-O— methylthiomethyladenosine N⁶-Acetyl-3',5'-O-(tetraisopropyldisiloxan-1,3-diyl)-adenosine (2.00 g, 3.62 mmol) was dissolved in 25 mL of dimethylsulfoxide, and 17.5 mL of acetic anhydride and 12.5 mL of acetic acid were added, and the reaction solution was stirred at room temperature for 14 hours. After the reaction completed, the reaction solution was added to 200 mL of water, extracted with ethyl acetate, and was washed with saturated aqueous sodium bicarbonate solution. The extract was dried over anhydrous sodium sulfate, and the solvent was distilled off. The obtained mixture was purified by silica gel column chromatography to obtain N⁶-acetyl-3',5'-O-(tetraisopropyldisiloxan-1,3-diyl)-2'-O-methylthiomethyl adenosine (1.36 g; yield 61%).

¹H-NMR (CDCl₃): 0.96-1.11 (m, 28H); 2.20 (s, 3H); 2.61 (s, 3H); 4.03 (dd, 1H, J=13.4, 2.4 Hz); 4.18 (d, 1H, J=9.1 Hz); 4.27 (d, 1H, J=13.4 Hz); 4.63-4.71 (m, 2H); 5.00 (d, 1H, J=11.5 Hz); 5.07 (d, 1H, J=11.5 Hz); 6.09 (s, 1H); 8.31 (s, 1H); 8.65 (s, 1H); 8.69 (s, 1H)

ESI-Mass: 635 [M+Na]⁺

Step 2

Production of N⁶-acetyl-3',5'-O-(tetraisopropyldisiloxan-1,3-diyl)-2'-O-(2-cyanoethoxymethyl)adenosine N⁶-Acetyl-3',5'-O-(tetraisopropyldisiloxan-1,3-diyl)-2'-O-methylthiomethyl adenosine (1.00 g, 1.63 mmol) obtained in step 1 was dissolved in 25 mL of tetrahydrofuran.

To the reaction solution was added 5.88 g of 3-hydroxypropionitrile (82.7 mmol), and the solution was dried by adding molecular sieves 4A, and was cooled to −45° C.

To the reaction solution was added 440 mg of N-iodosuccinimide (1.96 mmol) and then 490 mg of trifluoromethanesulfonic acid (3.26 mmol), and the reaction solution was stirred at −45° C. for 15 minutes. After the reaction completed, the reaction solution was neutralized by adding triethylamine while cooling, and diluted with methylene chloride. The reaction solution was washed with aqueous sodium thiosulfate solution and saturated aqueous sodium bicarbonate solution, the extract was dried over anhydrous sodium sulfate, and the solvent was distilled off. The obtained mixture was purified by silica gel column chromatography to obtain the objective compound (722 mg; yield 71%).

Example 16

Uridylyl-[3'→5']-uridylyl-[3'→5']-uridylyl-[3→5']-uridylyl-[3'→5']-uridylyl-[3'→5']-uridylyl-[3'→5']-uridylyl-[3'→5']-uridylyl-[3→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3→5']-uridylyl-[3'→5']-uridylyl-[3'→5']-uridine The oligo-RNA of the title compound was synthesized by entering commercially available CPG solid support (37 mg, 1 μmol) containing 2'/3'-O-benzoyl-5'-O-(4,4'-dimethoxytrityl)uridine to a column with a glass filter and using an automatic synthesizer for nucleic acid (Expedite™: Applied Biosystems). 5'-O-(4,4'-Dimethoxytrityl)-2'-O-(2-cyanoethoxymethyl)uridine 3'-O-(2-cyanoethyl N,N-diisopropylphosphoramidite) as a nucleic acid monomer compound, tetrazole as a condensation catalyst, iodine solution as an oxidizing agent, acetic anhydride and N-methylimidazole solution as a capping solution were used.

After condensing nucleic acid monomer compounds 20 times, the oligo-RNA was cleaved by reacting with 10 M aqueous ethanol solution of methylamine as a cleaving agent at room temperature for 1 to 2 hours, and the protecting groups of each phosphate part were removed.

After concentrating the reaction mixture under reduced pressure and removing unnecessary peaks with a reverse phase column (ODS), the reaction solution was purified with an eluent (acetonitrile-50 mM triethylamine-acetate buffer).

After concentrating the residue under reduced pressure, the residue was reacted with 1 M THF solution of tetrabutylammonium fluoride at room temperature for 1 hour to remove the 2'-hydroxyl protecting group.

After desalting the reaction solution, the protecting group of 5' end was removed with 80% acetic acid (treatment at room temperature for 10 minutes).

After concentrating under reduced pressure, the aqueous layer was washed with ether, and the high purity objective compound was obtained without purifying.

MALDI-TOF-MS:
Calculated 6367.52 [M+H]⁺
Found 6366.50 [M+H]⁺

It is clear from the analytical result with reverse phased HPLC of FIG. 1 that the obtained compound is of high purity.

Measurement Condition is as follows:
Measurement Condition
HPLC device
Unit for aspirating: LC-6A (SHIMADZU CORPORATION)
Detector: SPD-6A (SHIMADZU CORPORATION)

Reverse phased HPLC column: Mightysil RP-18GP <4.6 mm φ×15 cm> (KANTO KAGAKU)
Column temperature: 35° C.
Mobile phase gradient: Linear gradient, 20 min. (Solution B: 0%-70%)
Solution A: 50 mM triethylamine-acetate buffer including 5% acetonitrile
Solution B: 50 mM triethylamine-acetate buffer including 90% acetonitrile
A flow rate of a mobile phase: 1 ml/min.
Wavelength for detecting with ultraviolet-visible spectrophotometer: 260 nm Example 17

Cytidylyl-[3'→5']-uridylyl-[3'→5']-uridylyl-[3'→5']-adenylyl-[3'→5']-cytidylyl-[3'→5']-guanylyl-[3'→5']-cytidylyl-[3'→5']-uridylyl-[3→5']-guanylyl-[3'→5']-adenylyl-[3'→5']-guanylyl-[3'→5']-uridylyl-[3'→5']-adenylyl-[3→5']-cytidylyl-[3'→5']-uridylyl-[3'→5']-uridylyl-[3'→5']-cytidylyl-[3'→5']-guanylyl-[3→5']-adenylyl-[3'→5']-uridine The oligo-RNA of the title compound was synthesized by entering commercially available CPG solid support (37 mg, 1 μmol) containing 2'/3'-O-benzoyl-5'-O-(4,4'-dimethoxytrityl)uridine to a column with a glass filter and using a nucleic acid automatic synthesizer (Expedite™: Applied Biosystems) 5'-O-(4,4'-dimethoxytrityl)-2'-O-(2-cyanoethoxymethyl)uridine 3'-O-(2-cyanoethyl N,N-diisopropylphosphoramidite), N$^4$-acetyl-5'-O-(4,4'-dimethoxytrityl)-2'-O-(2-cyanoethoxymethyl)cytidine 3'-O-(2-cyanoethyl N,N-diisopropylphosphoramidite), N$^6$-acetyl-5'-O-(4,4'-dimethoxytrityl)-2'-O-(2-cyanoethoxymethyl)adenosine 3'-O-(2-cyanoethyl N,N-diisopropylphosphoramidite) and N$^2$-phenoxyacetyl-5'-O-(4,4'-dimethoxytrityl)-2'-O-(2-cyanoethoxymethyl)guanosine 3'-O-(2-cyanoethyl N,N-diisopropylphosphoramidite) as a nucleic acid monomer compound; 5-ethylthiotetrazole as a condensation catalyst; iodine solution as an oxidizing agent; phenoxyacetic anhydride and N-methylimidazole solution as a capping solution were used.

After condensing nucleic acid monomer compounds 19 times, the 5'-end hydroxyl protecting group was removed on the solid phase. Then, the oligo-RNA was cleaved by reacting with concentrated aqueous ammonia-ethanol mixture (3:1) as an cleaving agent at 40° C. for 4 hours, and the protecting groups of each phosphate part and base were removed.

After concentrating the reaction mixture under reduced pressure, the residue was reacted with 1 M THF solution of tetrabutylammonium fluoride containing 10% n-propylamine and 0.6% 2-mercaptoethylether at room temperature for 1 hour to removed the 2'-hydroxyl protecting group.

After desalting the reaction solution, the reaction solution was purified with DEAE-ion exchange resin (TOYOPEARL-DEAE-650) to obtain the high purity objective compound (112 OD$_{260}$; yield 58%).

Here, absorbance of ultraviolet in wavelength 260 nm (OD$_{260}$) shows a yield of an objective compound. Hereinafter, absorbance (OD$_{260}$) means a yield of an objective compound.

MALDI-TOF-MS:
Calculated 6305.9 [M+H]$^+$
Found 6304.8 [M+H]$^+$

Example 18

Adenylyl-[3'→5']-cytidylyl-[3'→5']-adenylyl-[3→5']-uridylyl-[3'→5']-cytidylyl-[3'→5']-adenylyl-[3'→5']-cytidylyl-[3'→5']-uridylyl-[3'→5']-uridylyl-[3'→5']-adenylyl-[3'→5']-cytidylyl-[3'→5']-guanylyl-[3'→5']-cytidylyl-[3→5']-uridylyl-[3'→5']-guanylyl-[3'→5']-adenylyl-[3'→5']-guanylyl-[3'→5']-uridylyl-[3→5']-adenylyl-[3'→5']-cytidylyl-[3'→5']-uridylyl-[3'→5']-uridylyl-[3'→5']-cytidylyl-[3→5']-guanylyl-[3'→5']-adenylyl-[3'→5']-adenylyl-[3'→5']-adenylyl-[3'→5']-uridylyl-[3→5']-guanylyl-[3'→5']-uridine The objective compound was synthesized in the same manner as Example 17 (92 OD$_{260}$; yield 31%).
MALDI-TOF-MS:
Calculated 9519.8 [M+H]$^+$
Found 9520.4 [M+H]$^+$ Example 19

Uridylyl-[3'→5']-uridylyl-[3'→5']-uridylyl-[3→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3→5']-uridylyl-[3'→5']-uridylyl-[3'→5']-uridylyl-[3→5']-uridylyl-[3'→5']-uridylyl-[3'→5']-uridylyl-[3→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3'→5']-uridylyl-[3→5']-uridylyl-[3'→5']-uridylyl-[3'→5']-uridylyl-[3→5']-uridylyl-[3'→5']-uridylyl-[3'→5']-uridylyl-[3→5']-uridylyl-[3'→5']-uridylyl-[3'→5']-uridylyl-[3→5' ]-uridylyl-[3'→5']-uridine The objective compound was synthesized in the same manner as Example 17 (254 OD$_{260}$; yield 65%).
MALDI-TOF-MS:
Calculated 12185.8 [M+H]$^+$
Found 12183.3 [M+H]$^+$ Example 20

Adenylyl-[3→5']-adenylyl-[3→5']-uridylyl-[3→5']-cytidylyl-[3→5']-adenylyl-[3→5']-cytidylyl-[3→5']-adenylyl-[3→5']-guanylyl-[3→5']-adenylyl-[3'→5']-adenylyl-[3→5']-uridylyl-[3'→5']-cytidylyl-[3→5']-guanylyl-[3→5']-uridylyl-[3'→5']-cytidylyl-[3→5']-guanylyl-[3→5']-uridylyl-[3'→5']-adenylyl-[3→5']-uridylyl-[3'→5']-guanylyl-[3→5']-cytidylyl-[3'→5']-adenylyl-[3'→5']-guanylyl-[3'→5']-uridylyl-[3'→5']-guanylyl-[3→5']-adenylyl-[3'→5']-adenylyl-[3'→5']-adenylyl-[3'→5']-adenylyl-[3'→5']-cytidylyl-[3'→5']-uridylyl-[3'→5']-cytidylyl-[3'→5']-uridylyl-[3'→5']-cytidylyl-[3'→5']-uridylyl-[3'→5']-uridylyl-[3'→5']-cytidylyl-[3'→5']-adenylyl-[3'→5']-adenylyl-[3'→5']-thymidine The objective compound was synthesized in the same manner as Example 17 (75 OD$_{260}$; yield 19%).
MALDI-TOF-MS:
Calculated 12731.8 [M+H]$^+$
Found 12731.7 [M+H]$^+$

Example 21

Uridylyl-[3'→5']-guanylyl-[3'→5']-adenylyl-[3'→5']-adenylyl-[3'→5']-uridylyl-[3'→5']-adenylyl-[3'→5']-cytidylyl-[3'→5']-adenylyl-[3'→5']-adenylyl-[3'→5']-adenylyl-[3'→5']-uridylyl-[3'→5']-cytidylyl-[3'→5']-adenylyl-[3'→5']-cytidylyl-[3'→5']-adenylyl-[3'→5']-guanylyl-[3'→5']-adenylyl-[3'→5']-adenylyl-[3'→5']-uridylyl-[3'→5']-cytidylyl-[3'→5']-guanylyl-[3'→5']-uridylyl-[3'→5']-cytidylyl-[3'→5']-guanylyl-[3'→5']-uridylyl-[3'→5']-adenylyl-[3'→5']-uridylyl-[3'→5']-guanylyl-[3'→5']-cytidylyl-[3'→5']-adenylyl-[3'→5']-guanylyl-[3'→5']-uridylyl-[3'→5']-guanylyl-[3'→5']-adenylyl-[3'→5']-adenylyl-[3'→5']-adenylyl-[3'→5']-adenylyl-[3'→5']-cytidylyl-[3'→5']-uridylyl-[3'→5']-cytidylyl-[3'→5']-uridylyl-[3'→5']-cytidylyl-[3'→5']-uridylyl-[3'→5']-uridylyl-[3'→5']-cytidylyl-[3'→5']-adenylyl-[3'→5']-adenylyl-[3'→5']-uridylyl-[3'→5']-uridylyl-[3'→5']-cytidylyl-[3'→5']-uridylyl-[3'→5']-uridylyl-[3'→5' ]-adenylyl-[3'→5']-thymidine The objective compound was synthesized in the same manner as Example 17 (83 $OD_{260}$; yield 15%).
MALDI-TOF-MS:
Calculated 17476.6 $[M+H]^+$
Found 17474.6 $[M+H]^+$

INDUSTRIAL APPLICABILITY

The phosphoramidite compound of the present invention has an ether-type protecting group which is introduced into the 2'-hydroxyl group. The ether-type protecting group is a linear protecting group and the steric structure around a phosphorus atom attached to the 3'-hydroxyl group is not crowded, and hence the phosphoramidite compound of the present invention makes it possible to proceed a condensation reaction in much shorter time and obtain a better condensation yield in the process of synthesizing an oligo-RNA as compared with a conventional phosphoramidite compound.

The use of the phosphoramidite compound of the present invention makes it possible to produce a high purity oligo-RNA using essentially the same method as in the production of an oligo-DNA.

All references cited and/or discussed in this specification are hereby incorporated by reference in their entireties and to the same extent as if each reference was individually incorporated by reference.

The invention claimed is:

1. A phosphoramidite compound represented by general formula (1),

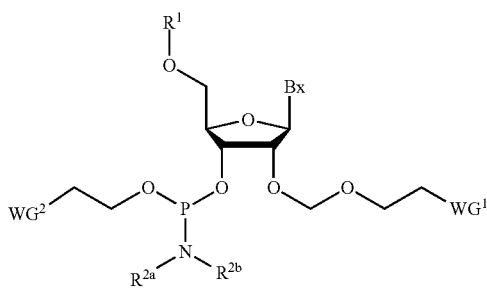

(1)

wherein:
$B_X$ represents a nucleobase optionally having a protecting group selected from the group consisting of benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene;
$R^1$ is a substituent represented by general formula (2),

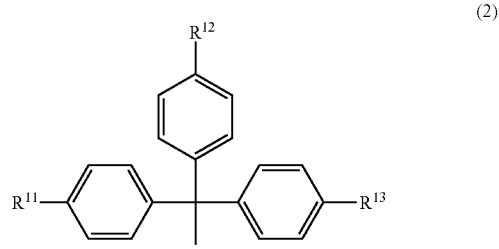

(2)

wherein:
$R^{11}$, $R^{12}$, and $R^{13}$ are the same or different and each represents hydrogen or C1-C4 alkoxy;
$R^{2a}$ and $R^{2b}$ are the same or different and each represents C1-C5 alkyl, or $R^{2a}$ and $R^{2b}$ taken together with the adjacent nitrogen atom represent pyrrolidine-1-yl, piperidine-1-yl, morpholine-1-yl, or thiomorpholine-1-yl; and
$WG^1$ and $WG^2$ are the same or different, $WG^1$ represents cyano, and $WG^2$ represents cyano, nitro, C1-C5 alkylsulfonyl, or halogen.

2. A ribonucleic acid compound represented by general formula (21),

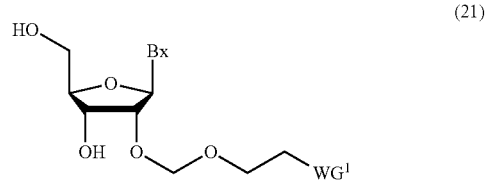

(21)

wherein:
$B_X$ represents a nucleobase optionally having a protecting group selected from the group consisting of benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene; and $WG^1$ represents cyano.

3. A ribonucleic acid compound represented by general formula (15),

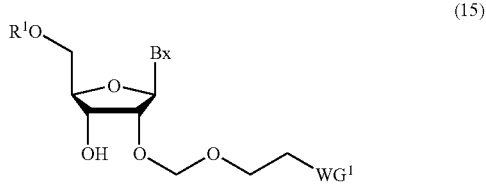

(15)

wherein:
$B_X$ represents a nucleobase optionally having a protecting group selected from the group consisting of benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene;

$R^1$ is a substituent represented by general formula (2),

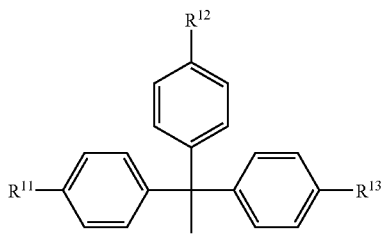
(2)

wherein:
$R^{11}$, $R^{12}$ and $R^{13}$ are the same or different and each represents hydrogen or C1-C4 alkoxy;
and
$WG^1$ represents cyano.

4. A ribonucleic acid compound represented by general formula (17),

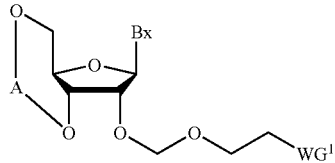
(17)

wherein:
$B_X$ represents a nucleobase optionally having a protecting group;
A represents a silicon substituent represented by general formula (18a) or (18b).

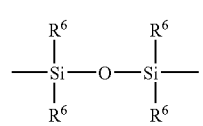
(18a)

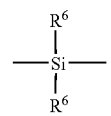
(18b)

wherein:
$R^6$ represents alkyl;
and
$WG^1$ represents cyano.

* * * * *

UNITED STATES PATENT AND TRADEMARK OFFICE
CERTIFICATE OF CORRECTION

PATENT NO.       : 8,691,970 B2                                                    Page 1 of 1
APPLICATION NO. : 11/574308
DATED            : April 8, 2014
INVENTOR(S)      : Ohgi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1048 days.

Signed and Sealed this
Twenty-ninth Day of September, 2015

Michelle K. Lee
*Director of the United States Patent and Trademark Office*